(12) United States Patent
Seth et al.

(10) Patent No.: US 7,642,265 B2
(45) Date of Patent: Jan. 5, 2010

(54) BENZIMIDAZOLES AND ANALOGS THEREOF AS ANTIVIRALS

(75) Inventors: Punit P. Seth, San Marcos, CA (US);
Elizabeth Anne Jefferson, La Jolla, CA (US); Richard H. Griffey, Vista, CA (US); Eric E. Swayze, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 139 days.

(21) Appl. No.: 10/946,757

(22) Filed: Sep. 22, 2004

(65) Prior Publication Data
US 2005/0165007 A1      Jul. 28, 2005

Related U.S. Application Data

(63) Continuation of application No. PCT/US03/38417, filed on Dec. 3, 2003.

(60) Provisional application No. 60/430,495, filed on Dec. 3, 2002.

(51) Int. Cl.
*A61P 31/12*     (2006.01)
*A61K 31/4188*   (2006.01)
*C07D 491/12*    (2006.01)

(52) U.S. Cl. .................... 514/257; 544/247

(58) Field of Classification Search ............. 514/257; 544/247
See application file for complete search history.

(56) References Cited

U.S. PATENT DOCUMENTS 3,863,414 A      2/1975   Dunn et al. ............... 423/109

FOREIGN PATENT DOCUMENTS

| DE | 888032       | 8/1953  |
| DE | 19916460 A1  | 10/2000 |
| GB | 1354554      | 5/1974  |
| WO | WO 00/56712  | 9/2000  |
| WO | WO 01/70705  | 9/2001  |

OTHER PUBLICATIONS

Csuk et al., "Chain extension of aldonolactones by samarium iodide-mediated Driedling-Schmidt reactions and samarium-assisted Imamoto reactions," *Tetrahedron* (1996) 52:9759-9776.
Agai et al., Databse CAPLUS on STN (Columbus, OH, USA), No. 85:78096, PCondensed 1,3,5,-triazepines. III. Derivatives of 4,5-dihydro-[1,3,5]triazepino1,2-a]benzimidazole, *Tetrahedron* 1976, vol. 32, No. 7, pp. 839-842, abstract, see RN 60078-74-2 and 60078-75-3 etc.
Edwards, Database CAPLUS on STN (Columbus, OH, USA), No. 79:18714, "Imidazole derivatives," 1973, abstract, DE 2259345, see RN 42032-10-0 and 42032-11-1.
Fonquerna et al., Database CAPLUS on STN (Columbus, OH, USA), No. 136:369609, "Preparation of dinolylpiperidines as antihistaminic and antiallergic agents," 2002, WO 2002-036589, see RN 423174-70-3 etc.
Freter et al., Database CAPLUS on STN (Columbus, OH, USA), No. 98:160710, "Substituted n-(4-indolylpiperidinoalkyl) benzimidazolones and their use as pharmaceutical preparations," 1983, abstract, EP 58975, see RN 84461-75-6.
Ogrua et al., Database CAPLUS on STN (Columbus, OH, USA), No. 77:160002, "Heterocyclic Compounds. 10. Synthesis of some imidazo[1,2-a]benzimidazoles with potent analgetic activities," *Journal of Medicinal Chemistry*, 1973, vol. 15, No. 9, pp. 923-926, abstract, see RN 38652-78-7 etc.
Teuber et al., Database CAPLUS on STN (Columbus, OH, USA), No. 132:93320, "Preparation of aminobenzimidazoles and guanidines as novel potassium channel blocking agents," 2000, WO 2000-001676, see RN 83750-38-3 etc.
Sarett et al., Database CAPLUS on STN (Columbus, OH, USA), No. 56:79451, "Benzimidazoles carrying thiazolyl, thiadiazolyl, and isothiazolyl substituents in the 2-position," 1962, US 3017415, abstract, see RN 91843-61-7.
Merck & Co., Database CAPLUS on STN (Columbus, OH, USA), No. 62:15351, "Substituted Benzimidazoles," 1964, GB 866796, abstract, see RN 4048-07-1.
E.R. Squibb and Sons, Inc., Database CAPLUS on STN (Columbus, OH, USA), No. 82:156304, "Pridyl-1H-Benzimidazole N-Oxide," 1975, abstract, US 3864350, see RN 55396-67-3.
Warner Lambert Co., Database CAPLUS on STN (Columbus, OH, USA), No. 108:131822, "Preparation and testing of antiarteriosclerotic substituted benzimidazol-2-yl- and 3H-imidazo[4,5-b]pyridine-2-ylphenoxyalkanoic acids and their salts and esters," 1988, US 4714762, abstract, see RN 113561-63-0.

(Continued)

*Primary Examiner*—Brenda L Coleman
(74) *Attorney, Agent, or Firm*—Isis Pharmaceuticals, Inc. Patent Department

(57) ABSTRACT

Provided are compounds of the formula:

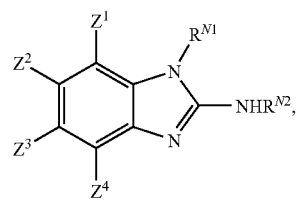

wherein $R^{N1}$ is a substituent of formula $G^1-NX^1X^2$, wherein $G^1$ is an optionally further substituted alkylene, which optionally forms, together with $R^{N2}$, a cyclic group, and each of $X^1$ and $X^2$ is independently H or an N-substituent, or $X^1$ and $X^2$ together form a heterocyclic ring, or $X^1$ together with $G^1$ forms a cyclic group and $X^2$ is H or an N-substituent; and each of $Z^1$, $Z^2$, $Z^3$ and $Z^4$ is H or a substituent, or two of $Z^1$, $Z^2$, $Z^3$ and $Z^4$ together form an optionally substituted ring, and further wherein at least one of $Z^1$, $Z^2$, $Z^3$ and $Z^4$ is other than H, and salts thereof, pharmaceutical compositions and methods of using the compounds. The compounds have antiviral activity.

20 Claims, 2 Drawing Sheets

OTHER PUBLICATIONS

Aventis Pharmaceuticals Products Inc., Database CAPLUS on STN (Columbus, OH, USA), No. 135:344381, "Preparation of 1-aroyl-piperidinyl benzamidines as inhibitors of factor Xa or tryptase," 2001, WO 2001-081310, abstract, see RN 370864-68-9.

International Search Report dated Jul. 28, 2004 for International Application No. PCT/US03/38093.

Hofstadler et al., "Mass spectrometry as a drug discovery platform against RNA targets," *Curr. Opin. Drug Discovery Dev.* (2000) 3:423-431.

Hofstadler et al., "Analysis of noncovalent complexes of DNA and RNA by mass spectrometry," *Chem. Rev.* (Washington, D.C.) (2001) 101:377-390.

Griffey et al., "Targeted site-specific gas-phase cleavage of oligoribonucleotides. Application in mass spectrometry-based identification of ligand binding sites," *J. Am. Chem. Soc.* (1999) 121:474-475.

Griffey et al., "Characterization of low-affinity complexes between RNA and small molecules using electrospray ionization mass spectrometry," *J. Am. Chem. Soc.* (2000) 122(41):9933-9938.

Griffey et al., Determinants of aminoglycoside-binding specificity for rRNA by using mass spectrometry, *Proc. Natl. Acad. Sci. USA* (1999) 96:10129-10133.

Ogura et al., "Studies on heterocyclic compounds. 10 Synthesis of some imidazol (1,2-a)benzimidazoles with potent analgetic activities," *J. of Medicinal Chemistry* (1972) 15(9):923-926.

Vlaovic et al., "Synthesis, antibacterial, and antifungal activities of some new benzimidazoles," *Bioscience, Biotechnology and Biochemistry* (1992) 56(2):199-206.

Chernova et al., *Khimiko-Farmasevticheski Zhurnai* (1991) 25(1):50-52.

Honda, M. et al., "A Phylogenetically Conserved Stem-Loop Structure at the 5' Border of the Internal Ribosome Entry Site of Hepatitis C Virus is Required for Cap-Independent Viral Translation," *J. Virol.* (1999) 73(2): 1165-1174.

Kieft, J. S. et al., "The Hepatitis C Virus Internal Ribosome Entry Site Adopts an Ion-dependent Tertiary Fold," *J. Mol. Biol.* (1999) 292(3): 513-529.

Kim, Y. K. et al., "Domains I and II in the 5' Nontranslated Region of the HCV Genome Are Required for RNA Replication," *Biochem. Biophys. Res. Comm.* (2002) 290(1): 105-112.

Lohmann, V. et al., "Replication of Subgenomic Hepatitis C Virus RNAs in a Hepatoma Cell Line," *Science* (1999) 285(5424): 110-113.

Sannes-Lowery, K. A. et al., "Measuring Dissociation Constants of RNA and Aminoglycoside Antibiotics by Electrospray Ionization Mass Spectrometry," *Anal. Biochem.* (2000) 280(2): 264-271.

Sannes-Lowery, K. A. et al., "Fourier transform ion cyclotron resonance mass spectrometry as a high throughput affinity screen to identify RNA binding ligands," *Trends Anal. Chem.* (2000) 19(8): 481-491.

Takeuchi, T. et al., "Real-Time Detection System for Quantification of Hepatitis C Virus Genome," *Gastroenterology* (1999) 116(3): 636-642.

Van De Loosdrecht, A. A. et al., "A tetrazolium-based colorimetric MTT assay to quantitate human monocyte mediated cytotoxicity against leukemic cells from cell lines and patients with acute myeloid leukemia," *J. Immunol Methods* (1994) 174(1-2): 311-320.

Yi, M. et al., "Subgenomic Hepatitis C Virus Replicons Inducing Expression of a Secreted Enzymatic Reporter Protein," *Virology* (2002): 304(2): 197-210.

Zhao, W. D. et al., "Genetic Analysis of a Poliovirus/Hepatitis C Virus Chimera: New Structure for Domain II of the Internal Ribosomal Entry Site of Hepatitis C Virus," *J. Virol.* (2001) 75(8): 3719-3730.

SEQUENCE LISTING

```
<160> NUMBER OF SEQ ID NOS: 2

<210> SEQ ID NO 1
<211> LENGTH: 161
<212> TYPE: RNA
<213> ORGANISM: Hepatitis C Virus

<400> SEQUENCE: 1
ccugugagga acuacugucu ucacgcagaa agcgucuagc cauggcguua guaugagugu      60
cgugcagccu ccaggggagg aacugcugga gacgcgcagc cuccggagga acuacuggag     120
acgugcagcc uccggaggaa cuagcgagag cugcagccuc c                         161

<210> SEQ ID NO 2
<211> LENGTH: 48
<212> TYPE: RNA
<213> ORGANISM: Hepatitis C Virus

<400> SEQUENCE: 2
gaggaacuac ugucuucacg caccgagagg ugagugucgu gcagccuc                   48
```

BENZIMIDAZOLES AND ANALOGS THEREOF AS ANTIVIRALS

CROSS REFERENCE TO RELATED APPLICATIONS

This application is a continuation of PCT/US2003/038417 filed Dec. 3, 2003, which claims benefit of Provisional Ser. No. 60/430,495 filed Dec. 3, 2002, each of which is incorporated herein by reference in its entirety.

FIELD OF THE INVENTION

The invention relates to benzimidazole derivatives having antiviral activity, to compositions of matter comprising the same, and to antiviral methods of using the same. The invention also contemplates assays and diagnostic methods employing benzimidazole derivatives according to the invention. In some embodiments, there are provided anti-HCV benzimidazoles.

BACKGROUND

Hepatitis C virus (HCV) is a hepatotropic, plus (+) strand RNA virus that presents a major threat to human health, infecting an estimated 170 million people worldwide. Acute HCV infection often leads to persistent infection, resulting in damage to the liver. Typical forms of liver damage caused by HCV include cirrhosis, chronic hepatitis and liver carcinoma. Less than 50% of patients respond to the current standard treatment, which is alpha interferon, alone or in combination with ribavirin. Accordingly, there has been intense interest in developing more efficacious anti-HCV drugs. It has been shown that the 5'-nontranslated region (5'-NTR) of the +RNA contains an internal ribosome entry site (IRES), which directs cap-independent initiation of virus translation. Furthermore, certain portions of the IRES element are essential for the HCV replication process. The IRES would appear to be a good target for antiviral compounds. Detailed descriptions of the HCV IRES and its functions have been presented, e.g. by Honda et al., in Journal of Virology, 73(2), 1165-74 (1999) (incorporated herein by reference, especially page 1166, Materials and Methods), and Kim, et al. in Biochem. Biophys. Res. Commun., 290, 105-112, (2002).

The activity of putative HCV IRES binding molecules can be measured using an HCV replicon per, e.g., the teaching of Lohmann et al. in Science, 285, 110-113 (1999) (incorporated herein by reference, especially page 111, FIG. 1 and legend thereof) and Yi, et al. in Virology, 304, 197-210 (2002).

Given the high infection rate of HCV worldwide, and given the relatively low efficacy of the standard therapeutic methods, there is a need for anti-HCV compounds, e.g. for use in HCV assays and anti-HCV prophylactic and therapeutic applications.

SUMMARY OF THE INVENTION

The foregoing and further needs are met by embodiments of the present invention, which provide anti-HCV compounds, compositions and methods of use. In some embodiments, there are provided compounds having anti-HCV activity as evinced by activity in the replicon assay as taught by Lemon et al., supra. In other embodiments, there are provided compositions comprising anti-HCV compounds, said compositions comprising an anti-HCV compound according to the present disclosure in admixture with one or more additives, e.g. diluents, excipients, adjuvants, etc. The present invention also provides methods of using anti-HCV compounds as described in more detail herein, said methods being directed toward attenuating expression of HCV RNA in vitro. The present invention also provides methods of using anti-HCV compounds as described in more detail herein, said methods being directed toward attenuating HCV in vivo. Some embodiments of the present invention provide compounds that inhibit HCV in the Lohman et al. replicon assay with $IC_{50}$ values in the low micromolar concentrations.

The present invention provides compounds having antiviral, and in particular anti-HCV activity. The present invention also provides compositions containing compounds of the formula I:

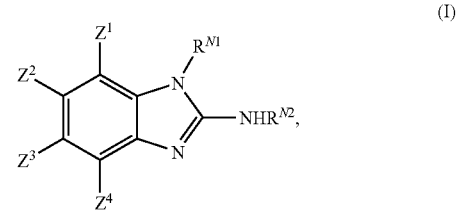

wherein $R^{N1}$ is a substituent of formula $G^1—NX^1X^2$, wherein $G^1$ is an optionally further substituted alkylene, which optionally forms, together with $R^{N2}$, a cyclo ring fused to the imidazole ring of the benzimidazole, and each of $X^1$ and $X^2$ is independently H or an N-substituent, or $X^1$ and $X^2$ together form a heterocyclic ring, or $X^1$ together with $G^1$ forms a cyclic group and $X^2$ is H or an N-substituent; and each of $Z^1$, $Z^2$, $Z^3$ and $Z^4$ is H or a substituent, or two of $Z^1$, $Z^2$, $Z^3$ and $Z^4$ together form an optionally substituted ring, and further wherein at least one of $Z^1$, $Z^2$, $Z^3$ and $Z^4$ is other than H. In some embodiments, compounds and compositions according to the present invention demonstrate HCV replicon assay $IC_{50}$ values in the low micromolar range.

The present invention further provides pharmaceutical compositions and methods of using the subject compounds as anti-HCV agents. In some embodiments, compounds of the invention may be used in HCV assays, in assays for measuring the relative efficacy of anti-HCV compounds or for treatment of HCV infection in vivo.

Methods for making the compounds of the invention are also disclosed. Other uses and advantages of embodiments of the present invention will be apparent to the person skilled in the art upon consideration of the disclosure, drawings and claims attached.

DETAILED DESCRIPTION OF THE INVENTION

Figure 1:
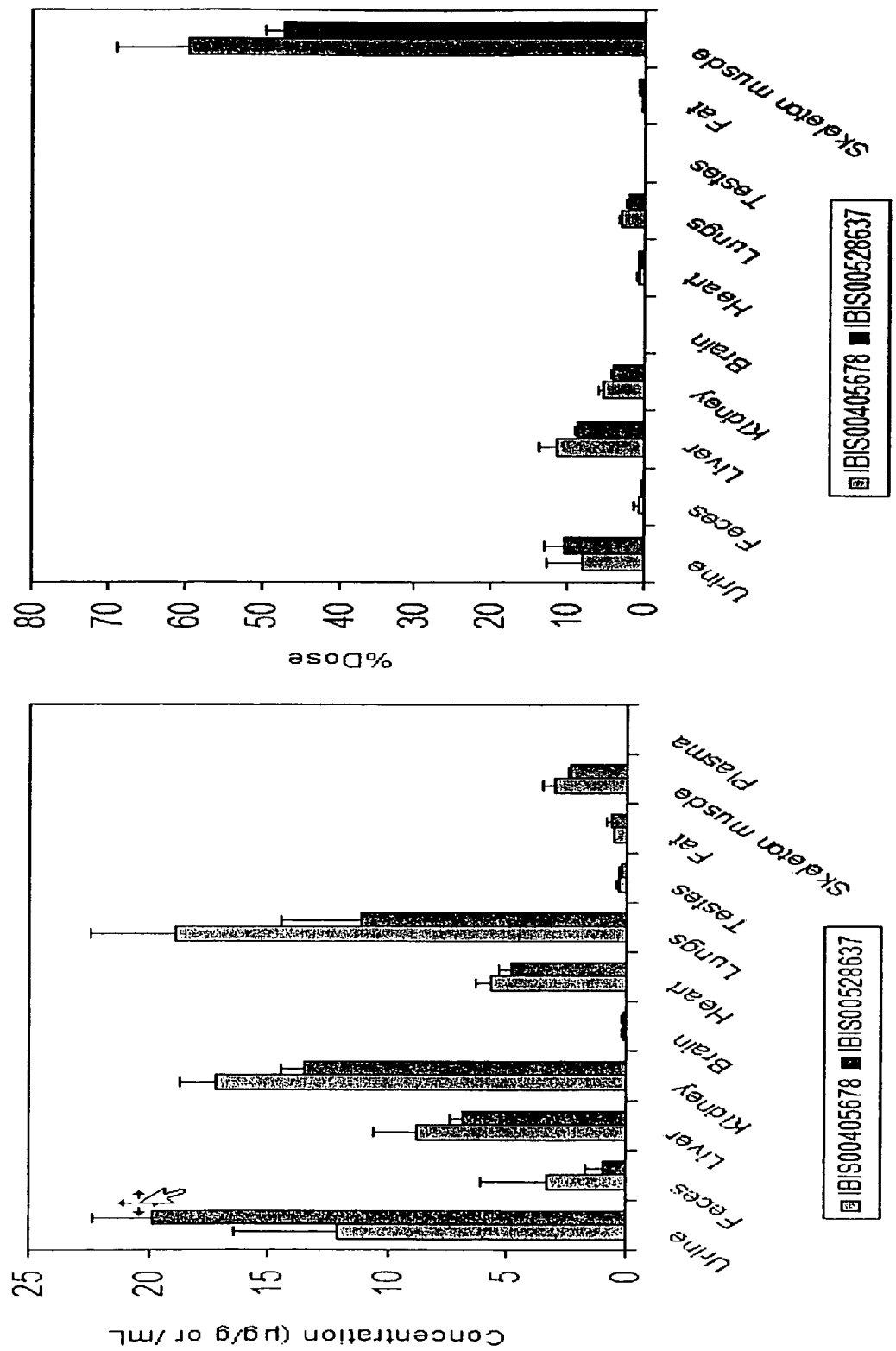
FIG. 1 is a bar graph of concentration of tested compounds in the presented tissues.

Provided are compounds of the formula:

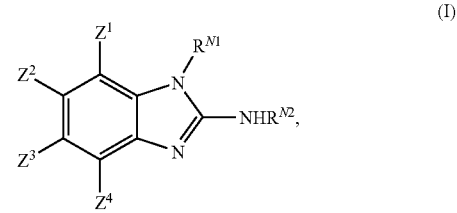

wherein $R^{N1}$ is a substituent of formula $G^1$—$NX^1X^2$, wherein $G^1$ is an optionally further substituted alkylene, which optionally forms, together with $R^{N2}$, a cyclic group, and each of $X^1$ and $X^2$ is independently H or an N-substituent, or $X^1$ and $X^2$ together form a heterocyclic ring, or $X^1$ together with $G^1$ forms a cyclic group and $X^2$ is H or an N-substituent; and each of $Z^1$, $Z^2$, $Z^3$ and $Z^4$ is H or a substituent, and wherein at least one of $Z^1$, $Z^2$, $Z^3$ and $Z^4$ is other than H.

In some embodiments, the present invention provides compounds of formula A:

(A)

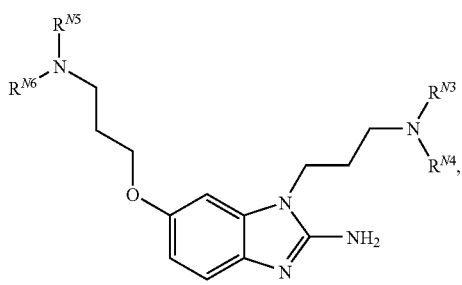

wherein each of $R^{N3}$ is H or a substituent, $R^{N4}$ is H or a substituent, or together $R^{N3}$ and $R^{R4}$ form a cyclic moiety that is optionally further substituted with one or more substituents; each of $R^{N5}$ is H or a substituent, $R^{N6}$ is H or a substituent, or together $R^{N5}$ and $R^{N6}$ form a cyclic moiety that is optionally further substituted with one or more substituents.

In some embodiments, the present invention provides compounds of formula B:

(B)

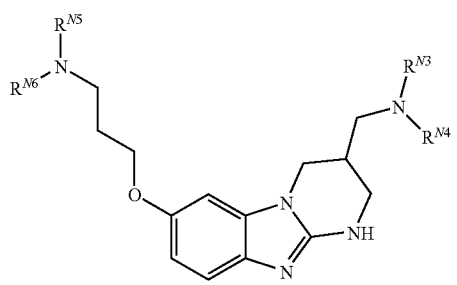

wherein $R^{N3}$ is H, a substituent, or together with the N to which it is attached forms guanidine, amidine, a substituted guanidine, or a substituted amidine; $R^{N4}$ is H, a substituent, or together with the N to which it is attached forms guanidine, amidine, a substituted guanidine, or a substituted amidine; or together $R^{N3}$ and $R^{N4}$ form a cyclic moiety that is optionally further substituted with one or more substituents; each of $R^{N5}$ is H or a substituent, $R^{N6}$ is H or a substituent, or together $R^{N5}$ and $R^{N6}$ form a cyclic moiety that is optionally further substituted with one or more substituents.

In some embodiments, the present invention provides compounds of formula C:

(C)

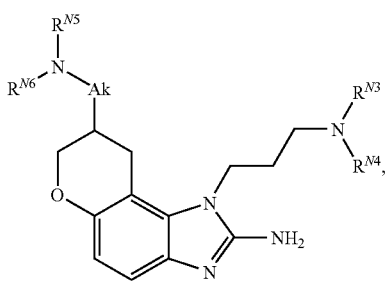

wherein Ak is $C_1$-$C_6$ alkylene, which is optionally further substituted; $R^{N3}$ is H or a substituent, $R^{N4}$ is H or a substituent, or together $R^{N3}$ and $R^{R4}$ form a cyclic moiety that is optionally further substituted with one or more substituents; each of $R^{N5}$ is H or a substituent, $R^{N6}$ is H or a substituent, or together $R^{N5}$ and $R^{N6}$ form a cyclic moiety that is optionally further substituted with one or more substituents.

In some embodiments, the present invention provides compounds of formula D:

(D)

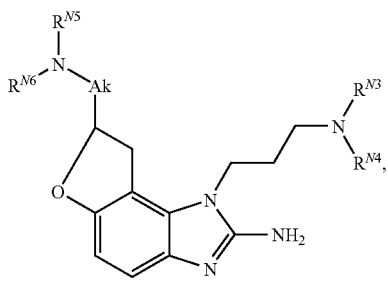

wherein Ak is $C_1$-$C_6$ alkylene, which is optionally further substituted; $R^{N3}$ is H or a substituent, $R^{N4}$ is H or a substituent, or together $R^{N3}$ and $R^{R4}$ form a cyclic moiety that is optionally further substituted with one or more substituents; each of $R^{N5}$ is H or a substituent, $R^{N6}$ is H or a substituent, or together $R^{N5}$ and $R^{N6}$ form a cyclic moiety that is optionally further substituted with one or more substituents.

In additional embodiments, the present invention provided compounds of the formula E:

(E)

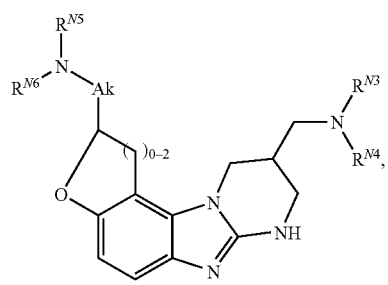

wherein Ak is $C_1$-$C_6$ alkylene, which is optionally further substituted; $R^{N3}$ is H or a substituent, $R^{N4}$ is H or a substituent, or together $R^{N3}$ and $R^{R4}$ form a cyclic moiety that is optionally further substituted with one or more substituents; each of $R^{N5}$ is H or a substituent, $R^{N6}$ is H or a substituent, or together $R^{N5}$ and $R^{N6}$ form a cyclic moiety that is optionally further substituted with one or more substituents.

Especially advantageous embodiments of the present invention provide compounds of the foregoing formulae I and A-E having antiviral activity, and especially anti-HCV activity, as discussed in more detail herein. In some embodiments, the compounds are used in vitro, e.g. in assays, kits or some other milieu, as test standards, e.g. for measuring the anti-HCV activity and/or potential of a candidate compound. In other embodiments, the compounds are used in vivo, e.g. as prophylactic or therapeutic compounds for the treatment of HCV infection, e.g. in humans.

In some embodiments, compounds of the foregoing formula in which, when $X^1$ or $X^2$ is further substituted alkyl, the further substituent does not comprise a 2-aminobenzimidazolyl moiety.

In further embodiments, there are provided compounds of the foregoing formula in which, when $X^1$ and $X^2$ form a ring, the ring is not a 2-aminobenzimidazol-1-yl ring.

In further embodiments, there are provided compounds of the foregoing formula in which neither $Z^2$ nor $Z^3$ is H, $CF_3$, unsubstituted $C_1$-$C_2$ alkyl, methoxy, ethoxy, or Cl.

In further embodiments, there are provided compounds of the foregoing formula in which $Z^3$ and $Z^4$ are not simultaneously methyl or Cl.

In further embodiments, there are provided compounds of the foregoing formula in which, when $X^1$ and $X^2$ are each alkyl (unsubstituted), $Z^2$ is neither methoxy nor N,N-dimethylaminopropyloxy.

In further embodiments, there are provided compounds of the foregoing formula in which, when $X^1$ and $X^2$ are each methyl or ethyl, $Z^2$ is not methoxy, ethoxy, or N,N-dialkylaminoalkyloxy.

Further preferred compound of the foregoing formula in which, when $X^1$ and $X^2$ are each methyl or ethyl, $Z^2$ is not neither methoxy nor N,N-dimethylaminopropyloxy.

In further embodiments, there are provided compounds of the foregoing formula in which, when $X^1$ and $X^2$ are each methyl, $Z^3$ is not aminomethyl or aminoethyl.

In further embodiments, there are provided compounds of the foregoing formula in which, when $X^1$ and $X^2$ are each methyl, $Z^2$ is not $C_1$-$C_2$ alkyl.

In further embodiments, there are provided compounds of the foregoing formula in which $Z^2$ and $Z^3$ are not simultaneously Cl.

It is to be understood that, when the compounds according to the present invention may be present either in their free base forms, as depicted in the formulae set forth herein, or as salts and/or hydrates thereof, and in particular as pharmaceutically acceptable salts thereof. Pharmaceutically acceptable salts are known in the art, as are hydrates, and the person having skill in the art will find it conventional to prepare such salts using art-recognized techniques. Exemplary salts include acid-addition salts, e.g. HCl, HBr, HI, $HNO_3$, $H_3PO_4$, $NaH_2PO_4$, $Na_2HPO_4$, $H_3PO_3$, $NaH_2PO_3$, $Na_2HPO_4$, $H_2SO_4$, $NaHSO_4$, carboxylic acids, such as acetic acid, malonic acid, capric acid, lauric acid, dichloroacetic acid, trichloroacetic acid, etc. Hydrates include hemihydrates, monohydrates, dihydrates, etc. Pharmaceutically acceptable salts include, HCl, $H_2SO_4$, acetic acid, malonic acid, capric acid, lauric acid, and other pharmacologically tolerated salts. Unless otherwise modified herein, the use of a free base formula is intended to include the salt and/or hydrate thereof.

As used herein, the term alkyl, unless otherwise modified, means an unsubstituted hydrocarbyl moiety. Acceptable alkyl groups include $C_1$-$C_{12}$ alkyl, especially $C_1$-$C_6$ alkyl, e.g. methyl, ethyl, isopropyl, n-propyl, n-butyl, t-butyl, s-butyl. Accordingly, unless otherwise modified, the term alkyl includes, when appropriate, branched and unbranched alkyl moieties.

As used herein, the term alkenyl, unless otherwise further modified, means an unsubstituted hydrocarbyl moiety having at least one double-bond unsaturation in the hydrocarbyl moiety. Acceptable alkenyl moieties are $C_2$-$C_{12}$, especially $C_2$-$C_6$ alkenyl, e.g. ethenyl, prop-1-enyl, prop-2-enyl, etc. Accordingly, unless otherwise modified, the term alkenyl includes, where appropriate, branched and unbranched, mono- and poly-unsaturated alkenyl moieties.

As used herein, the term alkynyl, unless otherwise further modified, means an unsubstituted hydrocarbyl moiety having at least one triple-bond unsaturation in the hydrocarbyl moiety. Acceptable alkynyl moieties are $C_2$-$C_{12}$, especially $C_2$-$C_6$ alkynyl, e.g. ethynyl, prop-1-ynyl, prop-2-ynyl, etc. Accordingly, unless otherwise modified, the term alkenyl includes, where appropriate, branched and unbranched, mono- and poly-unsaturated alkenyl moieties.

As used herein, the term cyclyl means a substituent group having at least one cyclic ring structure. The term embraces both carbocyclyl and heterocyclyl. In turn, the term carbocyclyl means a cyclic structure having only carbon in the ring. Heterocyclyl, on the other hand, means a cyclic structure having both carbon and at least one non-carbon atom in the ring. As used herein, cyclyl, carbocyclyl, and heterocyclyl include, when not further modified, include mono- and polycyclic structures. Also, as used herein, cyclyl, carbocyclyl and heterocyclyl, connote ring structures that are unsubstituted only, whereas optionally further substituted cyclyl, carbocyclyl and heterocyclyl ring structures are identified by appropriate use of a suitable modifier.

The term carbocyclyl includes fully saturated, partially unsaturated and fully unsaturated ring structures. The term cycloalkyl is synonymous with a fully saturated carbocyclyl. Partially unsaturated cycloalkyl means a carbocyclyl group having at least one unsaturation, but not having the full complement of unsaturations possible within the ring structure. Fully unsaturated cycloalkyl means a carbocyclyl group having the full complement of unsaturations possible within the ring structure. Aryl means a carbocyclyl substituent having at least one ring that possesses aryl ring character. Exemplary cycloalkyl groups include cyclopropyl, cyclobutyl, cyclopentyl, cyclohexyl, cycloheptyl, adamantyl, etc. Exemplary unsaturated cycloalkyl groups include cyclopentenyl, cyclohexenyl, cycloheptenyl, etc. Exemplary aryl groups include phenyl, naphthyl, 5,6,7,8-tetrahydronaphth-1-yl, etc.

The term heterocyclyl includes fully saturated, partially unsaturated and fully unsaturated ring structures. The term heterocyclyl also includes mon- and polycyclic ring structures in which at least one ring comprises carbon and at least one heteroatom in the ring. Exemplary heterocyclyl moieties have from one to three rings, comprise from one to about 14 carbons and from 1 to about 5 heteroatoms. Particular heterocyclyl moieties have from one to two rings and from one to about 10 carbons and from 1 to about 4 heteroatoms. Suitable heteroatoms include O, S and N. In particular embodiments, where necessary to satisfy its valence requirements, N may be unsubstituted (i.e. has an H to satisfy its valence of 3) or may be substituted with an alkyl or carbonyl, each of which may be further substituted. In particular embodiments, when such an N is substituted with alkyl, the alkyl is selected from methyl (Me) and ethyl (Et).

Fully saturated heterocyclyl includes pyrrolidinyl, piperidinyl, piperazinyl, N-alkyl piperazinyl, morpholino, N-alkylmorpholino, thiomorpholino, N-alkylthiomorpholino homopiperidinyl, homopiperazinyl, N-alkylhomopiperazinyl, homomorpholino, N-alkylhomomorpholino, homothiomorpholino, N-alkylhomothiomorpholino, tetrahydrofuranyl, tetrahydrothiophenyl, tetrahydrooxazolyl, N-alkyltetrahydrooxazolyl, tetrahydrothiazolyl, N-alkyltetrahydrothiazolyl, tetrahydroimidazolyl, N-alkyltetrahydroimidazolyl, etc.

Fully unsaturated heterocyclyl includes heteroaryl groups. Exemplary fully unsaturated heterocyclyl groups include pyrrolyl, imidazolyl, pyrenyl, pyridyl, pyrimidinyl, pyridazinyl, pyrazinyl, quinolyl, quoxalinyl, quinazolinyl, thiophenyl, furanyl, oxazolyl, thiazolyl, thiophenyl, pyranyl, thiopyranyl, benzofuranyl, indolyl, indazolyl, benzimidazolyl, benzothiazolyl, benzopyranyl, benzothiopyranyl, indazolyl, pyridopyrroly, etc. Partially unsaturated heterocyclyl includes partially unsaturated cognates of each of the following: pyrrolyl, imidazolyl, pyrenyl, pyridyl, pyrimidinyl, pyrazinyl, quinolyl, quoxalinyl, quinazolinyl, thiophenyl, furanyl, oxazolyl, thiazolyl, thiophenyl, pyranyl, thiopyranyl, benzofuranyl, indolyl, indazolyl, benzimidazolyl, benzothiazolyl, benzopyranyl, benzothiopyranyl, indazolyl, pyridopyrroly, etc.

Further substituents for cyclyl rings include halogens, e.g. Cl, Br and I, alkyl, alkenyl and alkynyl moieties, substituted alkyl, substituted alkenyl and substituted alkynyl moeities, wherein said further substituents are described herein. Further substituents for cyclyl rings also include further cyclyl rings, e.g. cycloalkyl, unsaturated cycloalkyl, fully unsaturated cycloalkyl, fully saturated heterocyclyl, partially unsaturated heterocyclyl, fully unsaturated heterocyclyl. Further substituents for cyclyl rings also include C(O)—R or C(O)O—R, wherein R is H, alkyl, or acyl, which alkyl may be further substituted. Further substituents for cyclyl rings also include $NO_2$, $NH_2$, NHR (where R is alkyl or may be further substituted), $NR_2$ (where R is alkyl or is further substituted), $OSO_3H_2$, $SO_3H_2$, OH, OR, wherein R is alkyl or acyl.

Further substituents for alkyl, alkenyl and alkynyl include halogens, e.g. Cl, Br and I, cyclyl rings, e.g. cycloalkyl, unsaturated cycloalkyl, fully unsaturated cycloalkyl, fully saturated heterocyclyl, partially unsaturated heterocyclyl, fully unsaturated heterocyclyl. Further substituents for alkyl, alkenyl and alkynyl also include C(O)—R or C(O)O—R, wherein R is H, alkyl, or acyl, which alkyl may be further substituted. Further substituents for cyclyl rings also include $NO_2$, $NH_2$, NHR (where R is alkyl or may be further substituted), $NR_2$ (where R is alkyl or is further substituted), $OSO_3H_2$, $SO_3H_2$, OH, OR, wherein R is alkyl or acyl.

Acyl groups include C(O)—R' groups, wherein R' is optionally substituted alkyl, alkenyl, alkynyl, cyclyl or O—R", wherein R" is H or R'. Especially suitable acyl groups include acetyl, benzoyl and t-butoxycarbonyl (BOC).

Alkylenyl means straight or branched divalent acyclic hydrocarbyl. Alkenylenyl means straight or branched divalent unsaturated hydrocarbyl, wherein at least one said unsaturations is a double bond. Alkynylenyl means straight or branched divalent acyclic hydrocarbyl having at least one triple bond unsaturation. Optionally further substituted alkylenyl, alkenylenyl or alkynenyl is an alkylenyl, alkenylenyl or alkynylenyl which has at least one additional substituent.

Replicon Assay: The Ntat2ANeo replicon containing cell line was obtained from Dr. S. Lemon at the University of Galvaston. Cells were grown, handled, treated with compound, and evaluated for HCV RNA levels as described previously (Yi, M.; Bodola, F.; Lemon, S. M. *Virology* 2002, 304, 197-210.) Briefly, the Ntat2ANeo cells were seeded into 96-well plates. The media was replaced 24 h later with fresh, G418-free media containing the indicated concentrations of drug. After the appropriate incubation period, cells were harvested, and quantitative RT-PCR assays were carried out using TaqMan chemistry on a PRISM 7700 instrument (ABI). For detection and quantitation of HCV RNA, primers complementary to the 5'-NTR region of HCV (Takeuchi, T., Katsume, A., Tanaka, T., Abe, A., Inoue, K., Tsukiyama-Kohara, K., Kawaguchi, R., Tanaka, S., and Kohara, M. *Gastroenterology* 1999, 116, 636-642.) were used. Results were normalized to the estimated total RNA content of the sample, as determined by the abundance of cellular GAPDH mRNA detected in a similar real-time RT-PCR assay using reagents provided with TaqMan GAPDH Control Reagents (Human) (Applied Biosystems).

MTT Toxicity Assay: The MTT cell proliferation assay was used to test our compounds for cell toxicity (v van de Loosdrecht, A. A.; Beelen, R. H.; Ossenkoppele, G. J.; Broekhoven, M. G.; Langenhuijsen, M. M. *J. Immunol. Methods* 1994, 174, 311-320. The assay kit was purchased from American Type Culture Collection (Manassas, Va., USA), and treatment of cells and the specific assay protocol was carried out according to the manufacturer's recommendations. The MTT cell proliferation assay measures cell viability and growth by the reduction of tetrazolium salts. The yellow tetrazolium salt is reduced in metabolically active cells to form purple formazan crystals which are solubilized by the addition of detergent. The color was quantified by spectrophotometric means. For each cell type a linear relationship between cell number and absorbance is established, enabling quantification of changes of proliferation.

EXAMPLES

In the Examples 1-12 of 2-aminobenzimidazoles are illustrated in Scheme 1:

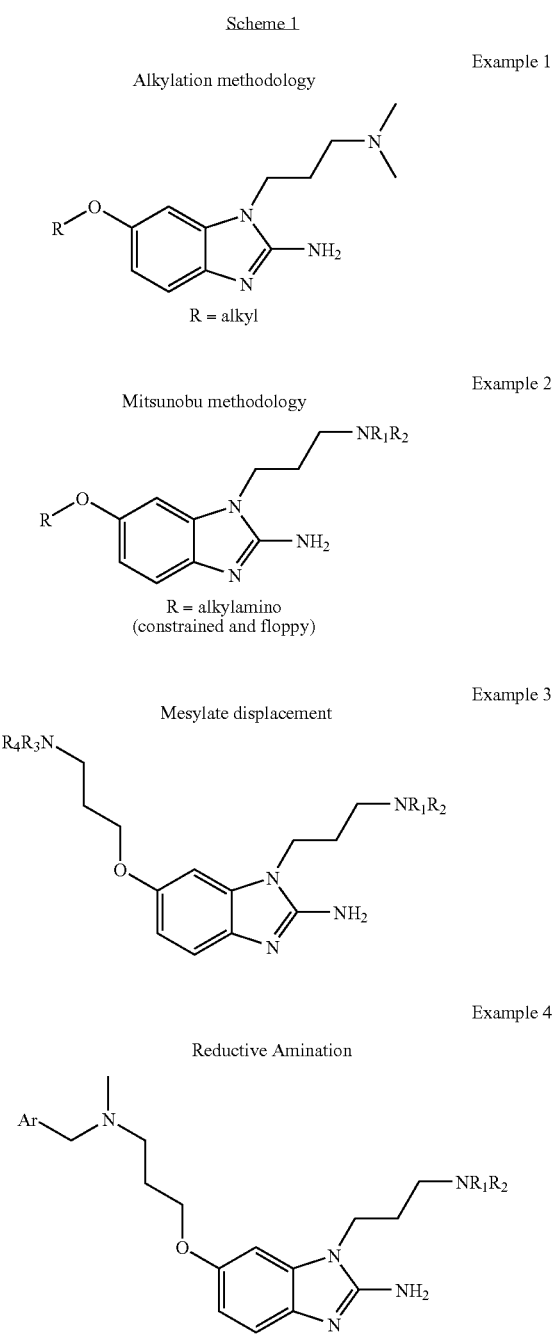

-continued

Example 5

Guanidine and mimetics

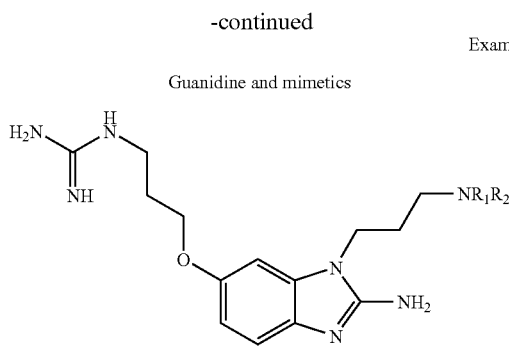

Example 6

Cyclic structures

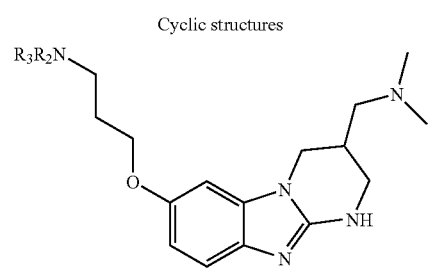

Example 7

Reductive Amination

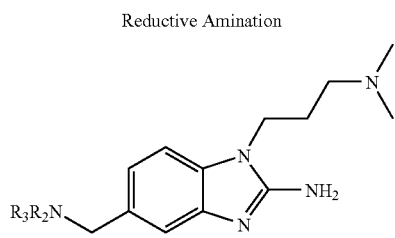

Example 8

Alkylation methodology

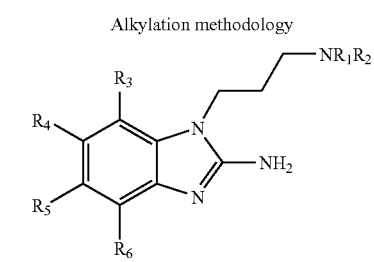

Example 9

SNAr methodology

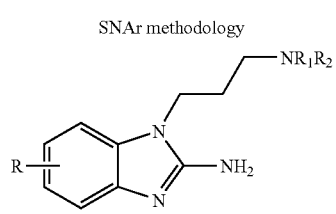

-continued

Example 10

Carbon tether analogs

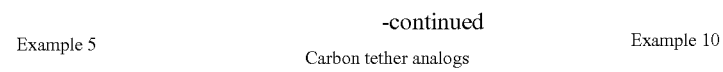

Example 11

C6 Sulfur analogs

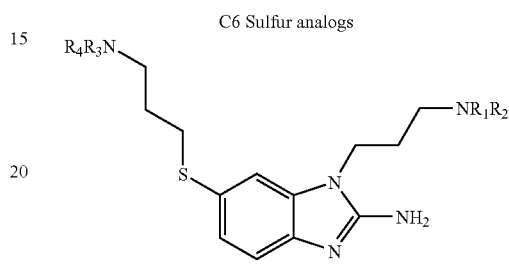

Example 12

Constrained structures

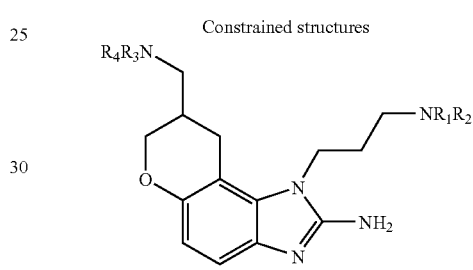

Example 15 and 16

Double Constrained Structures

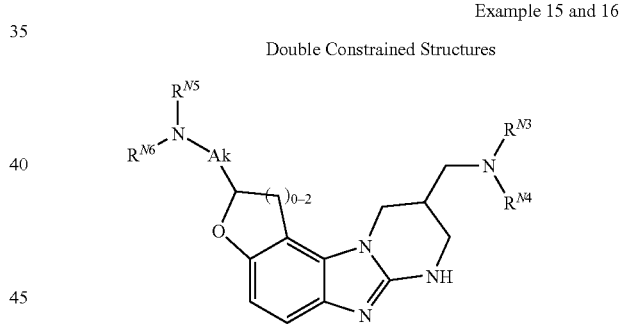

In each of the foregoing Examples 1-12 and 15 and 16 of Scheme 1, R, $R^1$, $R^2$, $R^3$, $R^4$, $R^5$, $R^6$ and $R^7$ are each, independently of the other, H or a substituent group. Exemplary substituent groups include alkyl, alkenyl, alkynyl, aryl, substituted alkyl, substituted alkenyl, substituted alkynyl or substituted aryl. Suitable alkyl groups include $C_1$-$C_{12}$, e.g. $C_1$-$C_6$ alkyl, such as methyl, ethyl, isopropyl, n-propyl, i-butyl, n-butyl, t-butyl, s-butyl, n-pentyl, etc. Suitable alkenyl groups include $C_2$-$C_{12}$, e.g. $C_2$-$C_6$ alkenyl, such as ethenyl, propen-3-yl, buten-4-yl, etc. Suitable alkynyl groups include $C_2$-$C_2$, e.g. $C_2$-$C_6$ alkynyl, such as ethynyl, prop-3-ynyl, etc. Suitable substituents include functional groups, such as $NO_2$, $NH_2$, COOH, halo, OH, $NH(C=NH)NH_2$, $NH(C=O)NH_2$, $NH(C=NH)H$, $CONH_2$, a substituted guanidine, amidine, a substituted amidine, etc. In each case where the functional group is an acid or a base group, the functional group may, together with a suitable counterion, form a salt, complex or chelate.

Example 1

Preparation of 6-alkoxy-2-amionbenzimidazoles

Example 1

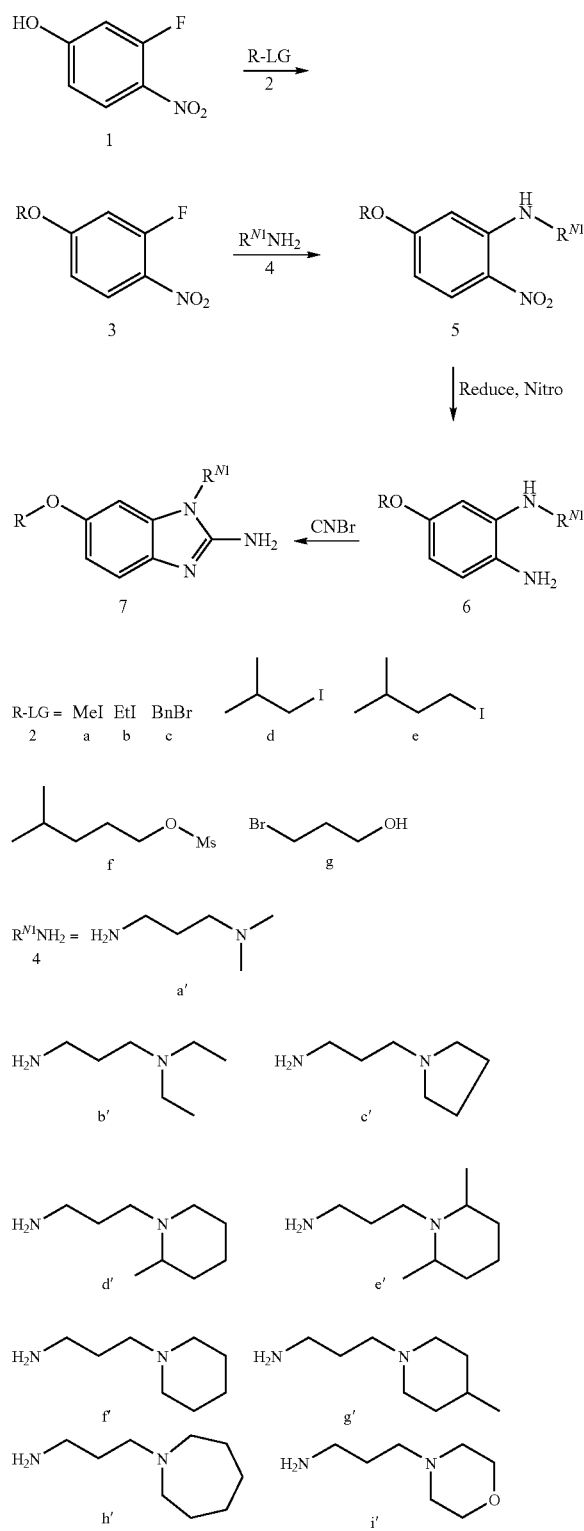

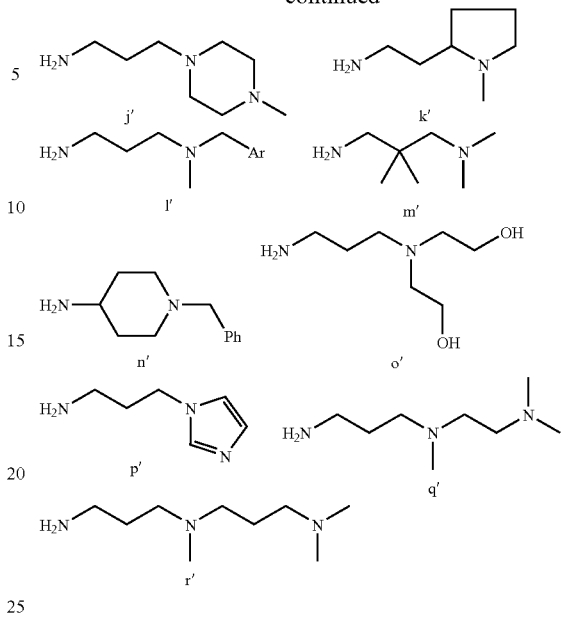

A mixture of 3-fluoro-4-nitrophenol 1 (3 mmol, 0.47 g), alkyl halide or alkylsulfonate 2 (3 mmol) and $K_2CO_3$ (3.3 mmol, 0.46 g) in acetone. (5 mL) was refluxed for 20 h. The reaction was then diluted with water and the aqueous layer was extracted with $CH_2Cl_2$ (twice). The combined organic layers were washed with water, brine, dried (over $MgSO_4$) and concentrated to provide 3.

Crude 3 was then dissolved in toluene (6 mL) and treated with $R^{N1}NH_2$ 4 (3.3-6 mmol) and $CaCO_3$ (3.6 mmol, 0.36 g) and the reaction was refluxed for 2 h. The reaction was diluted with water and extracted with EtOAc (2×). The combined organic layers were washed with water and brine, dried over $MgSO_4$ and concentrated to provide 5.

Crude 5 and 10% Pd/C (50 mg) were dissolved in EtOH (10 mL) and the mixture was hydrogenated at atmospheric pressure for 12 h at rt. The reaction was filtered through celite and concentrated to provide 6 as a dark oil.

Crude 6 obtained above was dissolved in EtOH (3 mL) and treated with CNBr (3.3 mmol, 0.35 g). The reaction was stirred for 12 h, after which it was diluted with 4M NaOH until strongly basic (pH>12) and extracted with $CH_2Cl_2$ (3×). The combined organic layers were washed with brine, dried over $MgSO_4$ and concentrated to provide 7 as a dark oil. Crude 7 could be purified by chromatography on aluminum oxide (activated, neutral, Brockmann 1, ~150 mesh) eluted with 5-10% MeOH/1% $NH_4OH/CH_2Cl_2$. Alternatively, crude 7 could also be purified by preparative reverse phase HPLC.

1-(3-Dimethylaminopropyl)-6-methoxy-1H-benzoimidazol-2-ylamine (7aa') was prepared according to the procedure described in Example 1 and purified by column chromatography to provide 7aa'. LCMS: LC retention time 1.22 min; MS ($ES^+$) 249.2 ($MH^+$).

3-[2-Amino-3-(3-dimethylaminopropyl)-3H-benzimidazoly-5-yloxy]-propan-1-ol (7ga') was prepared according to the procedure described in Example 1 and purified by column chromatography to provide 7ga'. LCMS: LC retention time 1.30 min.; MS ($ES^+$) 293.1 ($MH^+$).

Example 2

Synthesis of 6-alkylalkoxy-2-aminobenzimidazoles Using Mitsunobu Alkylation

Example 2

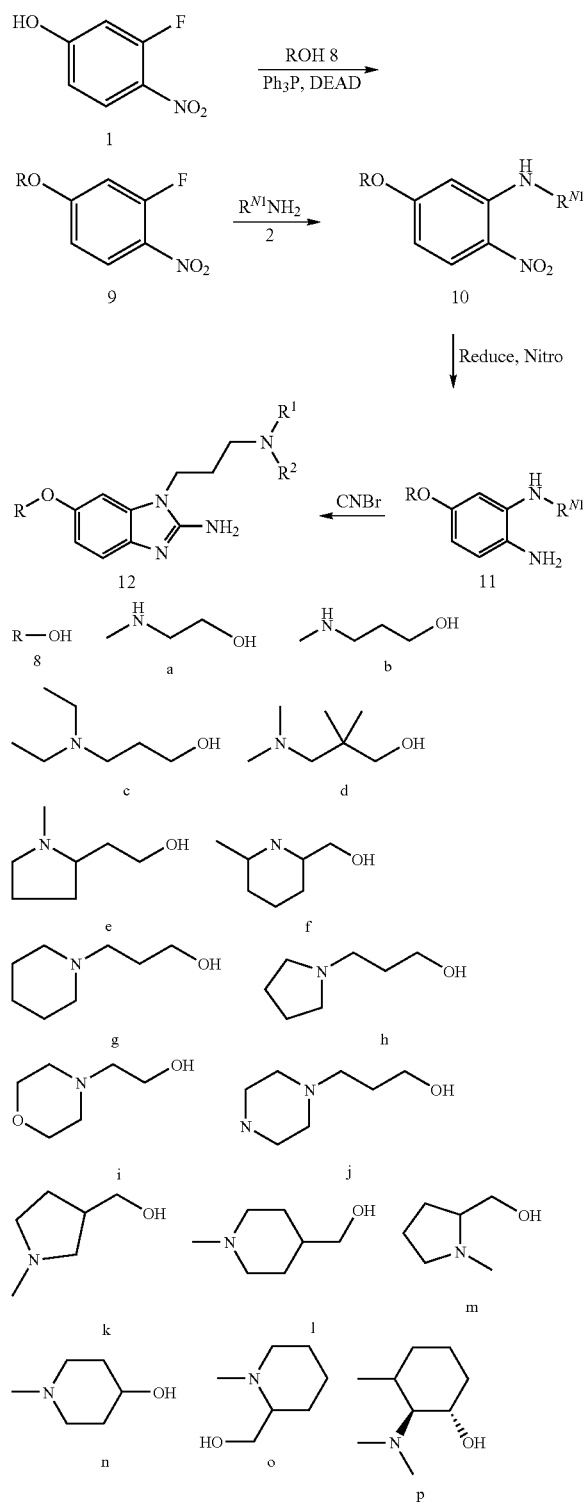

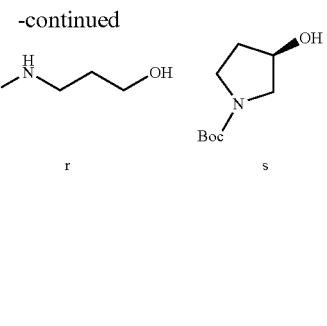

A mixture of 3-fluoro-4-nitrophenol 1 (8 mmol, 1.26 g), triphenyl phosphine (12 mmol, 3.14 g) and DIAD (12 mmol, 2.36 mL) in dry THF (70 mL) was cooled in an ice bath. Alcohol 8 (12 mmol) was added dropwise via a syringe to the above mixture and the reaction was stirred for 4 h. The solvent was then removed by concentration under vacuum to provide a thick oil, which was dissolved in $CH_2Cl_2$ and sequentially extracted with 1M NaOH, water and 10% HCl. The acidic aqueous layer was separated and washed with $CH_2Cl_2$ and basified (pH>12) using solid NaOH and then further extracted with EtOAc. The EtOAc layer was then separated and washed with brine, dried and concentrated to provide crude 9 along with some (5-30%) DIAD byproduct.

Crude 9 obtained above was dissolved in toluene (20 mL) and treated with amine 4 (10-15 mmol) and $K_2CO_3$ (10 mmol, 1.38 g) and the reaction was refluxed for 2 h. The reaction was diluted with water and extracted with EtOAc (2×). The combined organic layers were washed with water and brine, dried over $MgSO_4$ and concentrated to provide 10.

Crude 10 obtained above and 10% Pd/C (100-200 mg) were dissolved in EtOH (10 mL) and the mixture was hydrogenated at atmospheric pressure for 12 h at room temperature. The reaction was filtered through celite and concentrated to provide 11 as a dark oil.

Crude 11 obtained above was dissolved in EtOH (10 mL) and treated with CNBr (10 mmol, 1.06 g). The reaction was stirred for 12 h, after which it was diluted with 4 M NaOH until strongly basic (pH>12) and extracted with $CH_2Cl_2$ (3×). The combined organic layers were washed with brine, dried over $MgSO_4$ and concentrated to provide 12 as a dark oil. Crude 12 could be purified by chromatography on aluminum oxide (activated, neutral, Brochmann 1, ~150 mesh), eluting with 5-10% MeOH/1% $NH_4OH/CH_2Cl_2$. Alternatively, crude 12 could also be purified by preparative reverse phase HPLC.

1-(3-Dimethylaminopropyl)-6-(3-piperidin-1-ylpropoxy)-1H-benzimidazol-2-ylamine (12ga') was prepared according to the procedure described in Example 2, and purified by preparative reverse phase HPLC to provide 159 mg of 12ga'•3TFA. LCMS: LC retention time 0.96 min.; MS (ES$^+$) 348.1 (MH$^+$).

1-(3-Dimethylaminopropyl)-6-(2-morpholin-4-ylethoxy)-1H-benzoimidazol-2-ylamine (12ia') was prepared according to the procedure described in Example 2 and purified by preparative reverse-phase HPLC to provide 100 mg of 12ia'•3TFA. LCMS: LC retention time 0.51 min.; MS (ES$^+$) 348.1 (MH$^+$).

Example 3
Synthesis of 6-alkylaminoalkoxy-2-aminobenzimidazoles by Mesylate Displacement
Example 3
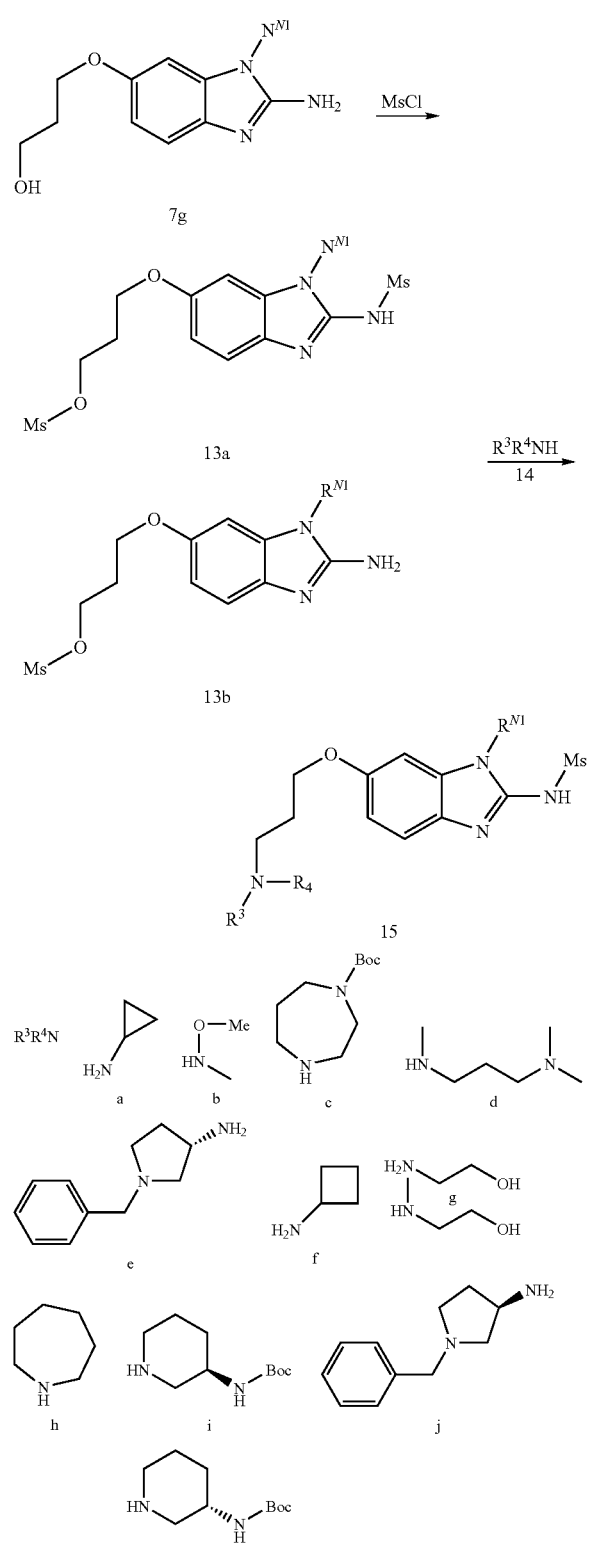
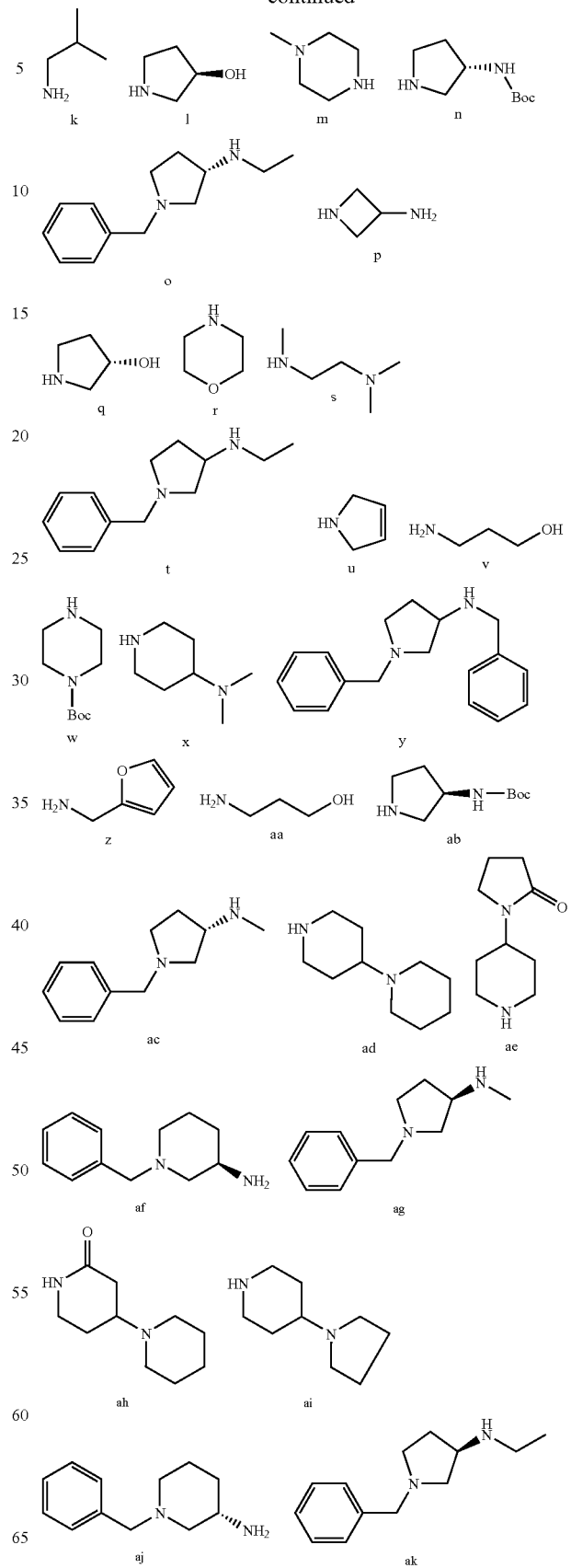

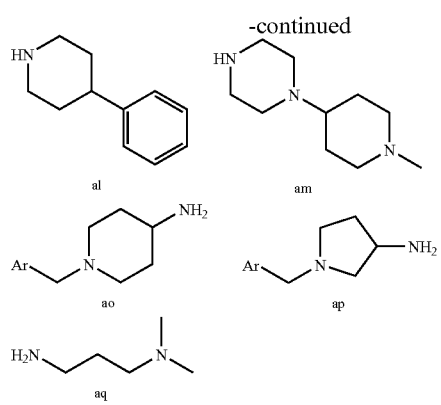

al
am
ao
ap
aq

A mixture of 2-aminobenzimidazole 7 g (14.3 mmol, 4.3 g), 4-dimethylaminopyridine (1.4 mmol, 0.17 g) and $K_2CO_3$ (35.8 mmol, 4.94 g) in $CH_2Cl_2$ (15 mL) was cooled in an ice bath. Methanesulfonyl chloride (31.5 mmol, 2.43 mL) was added dropwise via a syringe to the above mixture and the reaction was stirred for an additional 3 h. The reaction was then diluted with $CH_2Cl_2$ and the organic phase was washed with water, then with brine, then was dried over $MgSO_4$ and concentrated to provide a mixture of 13a and 13b in varying ratios. The crude mixture of 13a and 13b thus obtained was dissolved in DMF (40 ML) and this solution was distributed into 40 vials (1 mL each). $K_2CO_3$ (0.75 mmol., 0.103 g) and the desired primary or secondary amine (0.75 mmol-0.88 mmol) was added to each reaction vessel. The individual reactions were heated at 60° C. for 14 h, after which the contents of each vessel were diluted with $CH_2Cl_2$ and the organic layer was washed with 4M NaOH, washed with brine, then dried over $MgSO_4$ and concentrated to provide crude 15, which was further purified by preparative reverse phase HPLC.

When the final product 15 contained a Boc protecting group, crude 15 was dissolved in a mixture of $CH_2Cl_2$/TFA (1:1, 2 mL). The reaction was stirred overnight and then concentrated, and the residue was purified by preparative reverse-phase HPLC (rpHPLC).

N-{3-(2-Amino-3-(3-dimethylaminopropyl)-3H-benzimidazol-5-yloxy]propyl}-N,N',N'-trimethylpropane-1,3-diamine (15da') was prepared according to the procedure described in Example 3 and purified by preparative rpHPLC to provide 68 mg of 15da'•3TFA. LCMS: LC retention time 0.38 min.; MS (ES$^+$) 391.2 (MH$^+$).

N-{3-[2-Amino-3-(3-dimethylaminopropyl)-3H-benzoimidazol-5-yloxypropyl}-N,N',N'-trimethylethane-1,2-diamine (15sa') was prepared according to the procedure described in Example 3 and purified by preparative rpHPLC to provide 81 mg of 15sa'•3TFA. LCMS: LC retention time 0.40 min.; MS (ES$^+$) 377.2 (MH$^+$).

Example 4

Synthesis of 6-alkylaminoalkoxy-2-aminobenzimidazoles by Reductive Amination

Example 4

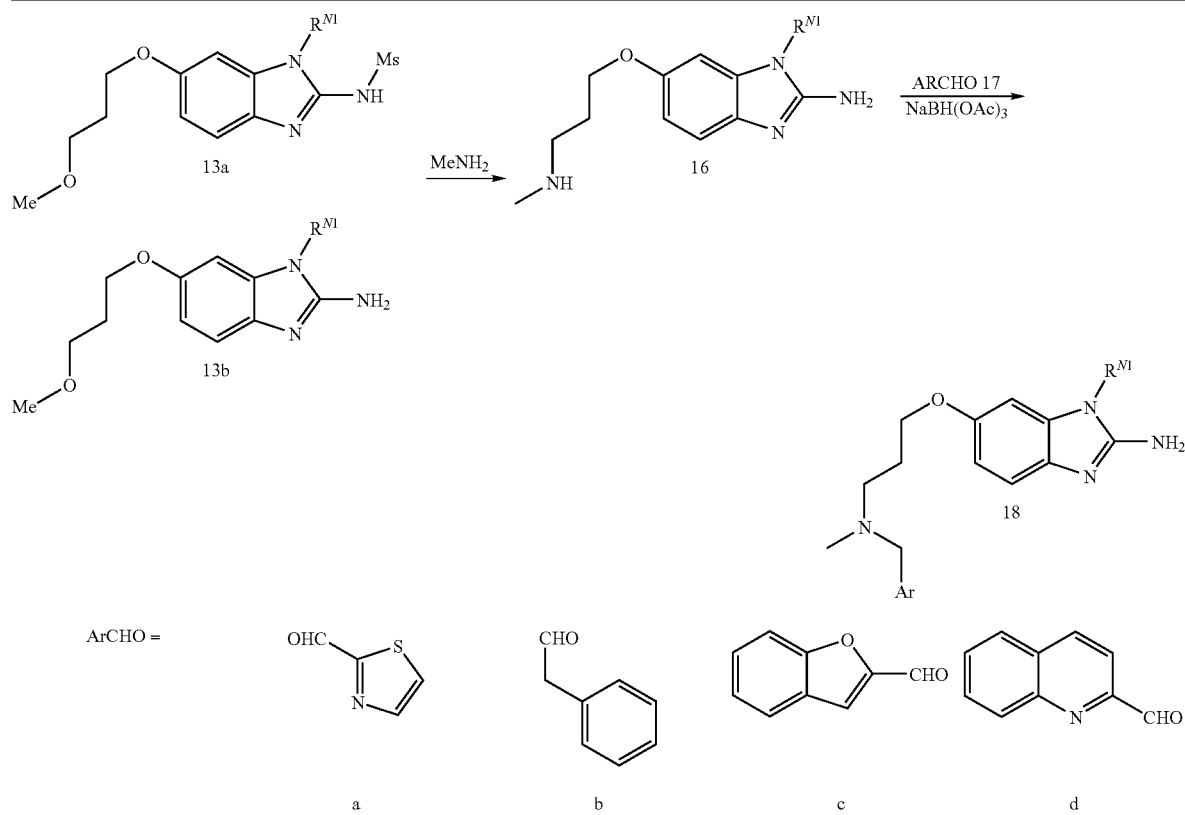

-continued
| | | | | |
|---|---|---|---|---|
| 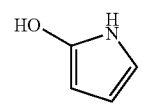 | 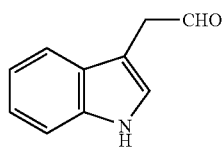 | 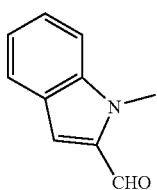 | 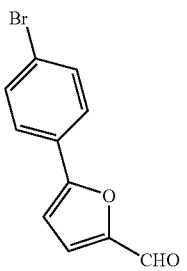 | 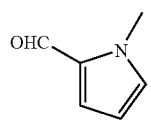 |
| e | f | g | h | i |
| 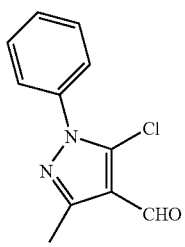 | 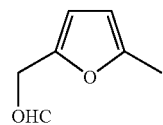 | 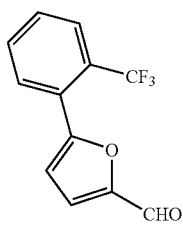 | 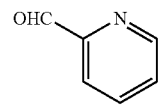 | 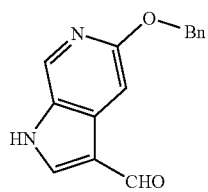 |
| j | k | l | m | n |
| 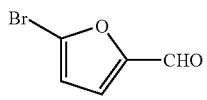 | 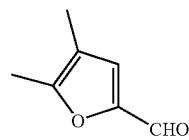 | 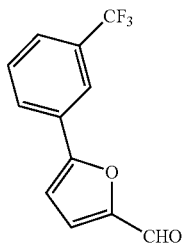 | 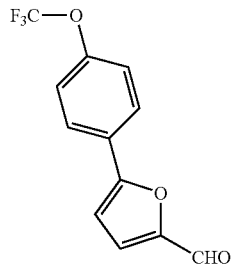 | 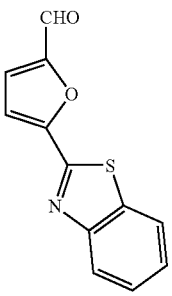 |
| o | p | q | r | s |
| 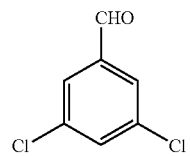 | 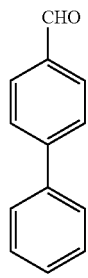 | 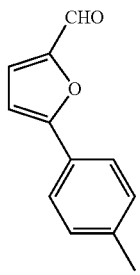 | 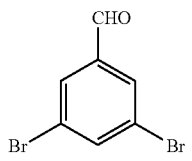 | 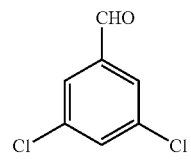 |
| t | u | v | w | x |
| 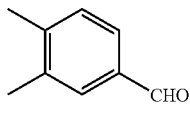 | 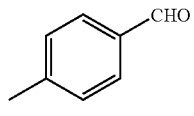 | 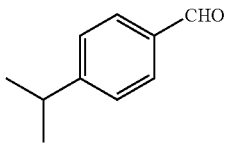 | 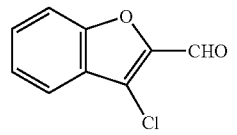 | 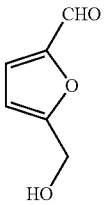 |
| y | z | aa | ab | ac |

A mixture of 2-aminobenzimidazole 7b (7.15 mmol, 2.15 g), 4-dimethylaminopyridine (0.7 mmol, 0.085 g) and $K_2CO_3$ (18 mmol, 2.47 g) in $CH_2Cl_2$ (8 mL) was cooled in an ice bath. Methanesulfonyl chloride (14.3 mmol, 1.2 mL) was added dropwise via a syringe to the above mixture and the reaction was stirred for an additional 3 h. The reaction was then diluted with $CH_2Cl_2$ and the organic phase was washed with water, then with brine, and then dried over $MgSO_4$ and concentrated to provide a mixture of 13a and 13b in varying ratios. The crude mixture of 13a and 13b obtained above was then dissolved in DMF (31 mL) and treated with methylamine (15 mL of a 40% solution in $H_2O$) and heated at 60° C. in a sealed vessel for 12 h. The reaction was cooled and diluted with saturated $Na_2CO_3$ and extracted with $CH_2Cl_2$ (3×). The combined organic layers were washed with brine, and then dried over $MgSO_4$ and concentrated to provide crude 2-aminobenzimidazole 16 as a dark, red oil (1 g).

Proton data for 16a': $^1$H NMR (200 MHz, $CDCl_3$) δ 7.24 (d, 1H), 6.7 (dd, 1H), 6.6 (d, 1H), 5.8 (s, br, 2H), 4.05 (t, 2H), 4.0 (m, 2H), 2.8 (t, 2H), 2.42 (s, 3H), 2.2 (s, 6H), 2.1 (m, 2H), 1.95 (m, 4H). LCMS: LC retention time 0.44 min.; MS ($ES^+$) 306.2 ($MH^+$).

Crude 2-aminobenzimidazole 16 obtained above (0.33 mmol, 0.1 g) and the desired aldehyde 17 (0.33 mmol) was dissolved in dry $CH_2Cl_2$ (2 mL). Glacial acetic acid (1 drop) was added to the reaction, which was stirred for 5-10 min., followed by addition of sodium triacetoxyborohydride (0.66 mmol, 0.14 g). The mixture was stirred at room temperature for 12 h, after which it was diluted with $CH_2Cl_2$ and the organic phase was washed with saturated $Na_2CO_3$, then with brine, and then was dried over $MgSO_4$ and concentrated. Crude 2-aminobenzimidazole 18 thus obtained was further purified by preparative rpHPLC.

6-[3-Methyl-pyridin-2-ylmethylamino)-propoxy]-1-(3-pyrrolidin-1-ylpropyl)-1-benzimidazol-2-ylamine (18mc') was prepared according to the procedure described in Example 4 and purified by preparative reverse phase HPLC to provide 30 mg of 18mc'•3TFA. LCMS: LC retention time 1.46 min. MS ($ES^+$) 423.1 ($MH^+$).

1-[2-Methyl-piperidin-1-yl)propyl]-6-{3-[methyl-1H-pyrrol-2-ylmethyl)-amino]-propoxy}-1H-benzimidazol-2-ylamine (18ed') was prepared according to the procedure described in Example 4 and purified by preparative rpHPLC to provide 73 mg of 18ed'•3TFA. LCMS: LC retention time 1.63 min.; MS ($ES^+$) 439.2 ($MH^+$).

Example 5

Synthesis of 6-guanidinoalkoxy-2-aminobenzimidazoles

Example 5

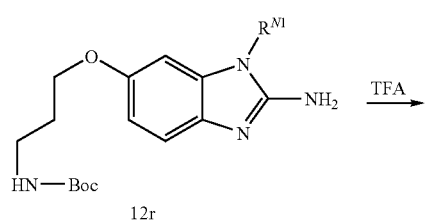

12r

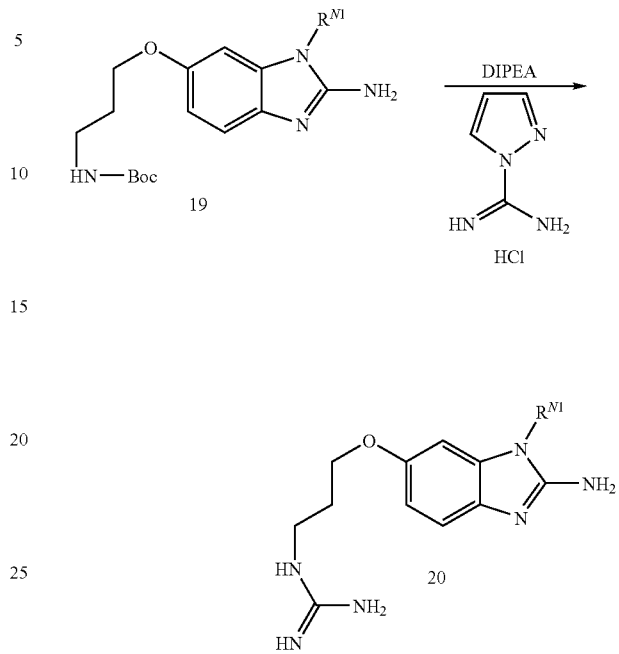

2-aminobenzimidazole 12r was prepared as per the procedure described in Example 2, except that the acid-base extraction after the Mitsunobu alkylation (step 1) was replaced by column chromatography. Also, the cyanogens bromide cyclization was carried out in the presence of $K_2CO_3$ (2 eq.). Purification by chromatography on silica gel (15% MeOH/1% $Et_3N/I$) provided 12r.

Purified 12r obtained above was dissolved in a mixture of $CH_2Cl_2$ (5 mL) and TFA (5 mL) and the reaction was stirred at room temperature for 12 h. The reaction was concentrated under vacuum and the residue was dissolved in $CH_2Cl_2$ and the organic phase was washed with 4M NaOH and then with brine, after which it was dried over $MgSO_4$ and concentrated to provide crude 19.

A solution of crude 19 and DIPEA (0.25 mmol, 0.032 mL) in DMF (0.3 mL) was cooled in an ice bath and 1H-pyrazole-1-carboxamidine hydrochloride (0.25 mmol, 0.037 g) was added as a solid to the reaction. After stirring for 12 h at room temperature, the reaction was diluted with $CH_2Cl_2$ and washed with 4M NaOH and then with brine, after which it was dried over $MgSO_4$ and concentrated to provide guanidine 20, which was purified by preparative rpHPLC.

N-{3-[2-dimethylamino-propyl)-3H-benzoimidazol-5-yloxy]-propyl}-guanidine (20a') was prepared according to the procedure described in Example 5 and purified by preparative rpHPLC to provide 20.5 mg of 20a'•3TFA. LCMS: LC retention time 0.63 min.; MS ($ES^+$) 334.1 ($MH^+$). $^1$H NMR (200 MHz, $CD_3OD$) δ7.3 (d, 1H), 7.2 (d, 1H), 6.95 (dd, 1H), 4.2 (m, 4H), 3.4 (t, 2H), 3.2 (m, partially overlapped 2H), 2.95 (s, 6H), 2.24 (m, 2H), 2.15 (m, 2H).

Example 6

Synthesis of N1-N2 cyclic 2-aminobenzimidazoles

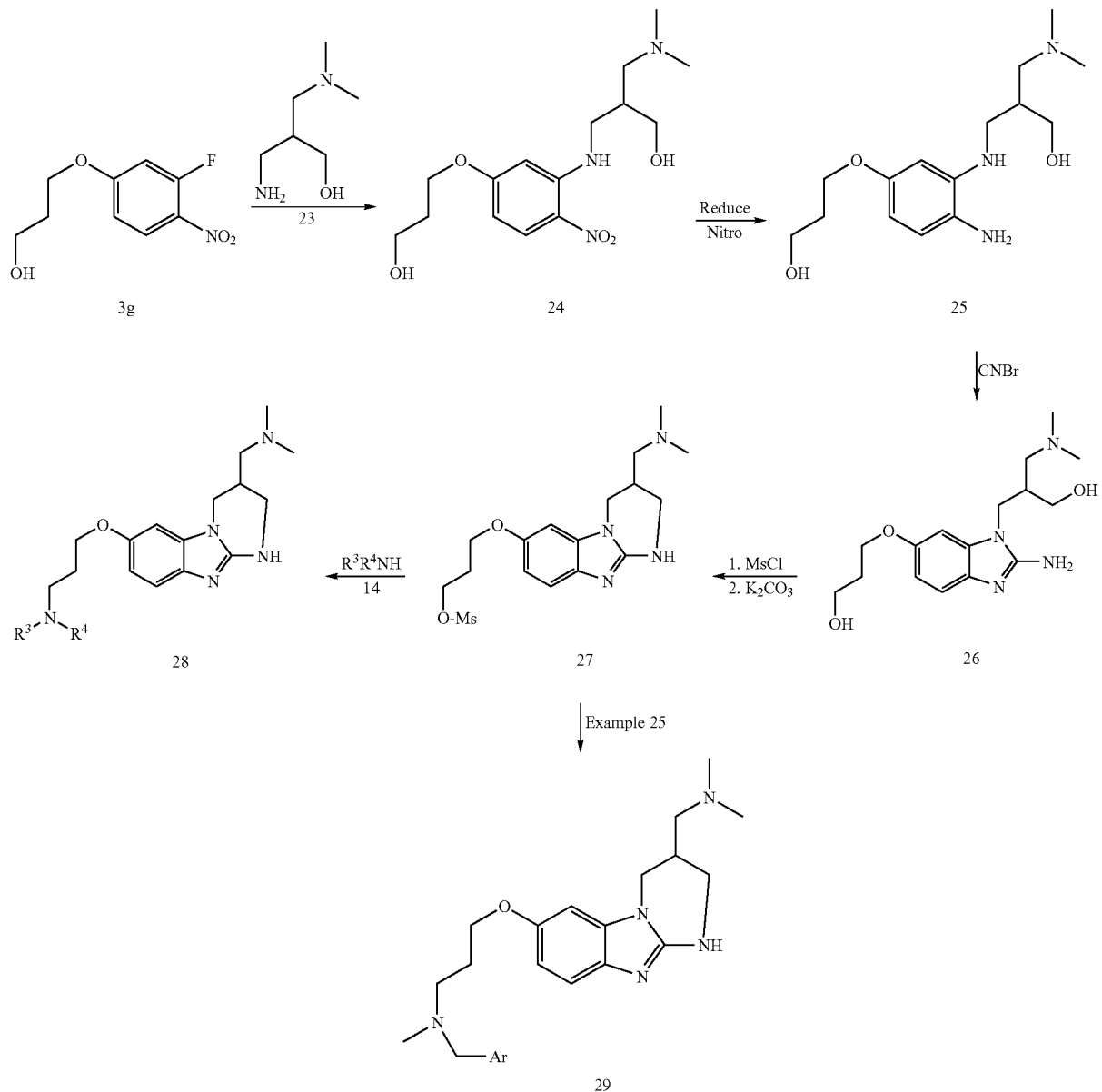

2-hydroxymethyl-acrylonitrile (37 mmol, 3.1 g, prepared as per procedure described by Csuk et al. in *Tetrahedron*, 1996, 52, 9759-9776) was treated with dimethylamine (25 mL of a 2M solution in THF) and the reaction was heated in a sealed vessel at 45° C. for 14 h. The reaction was cooled to room temperature and all the volatiles were removed by concentration under vacuum. The crude 2-hydroxymethyl-3-dimethylaminopropionitrile thus obtained was dissolved in dry THF (50-60 mL) and this solution was added dropwise to a cold (−78° C.) suspension of LAH (6 g) in THF (300 ML). The reaction was gradually warmed to room temperature and stirred for an additional 12 h at room temperature. The reaction was then cooled in an ice bath and very carefully quenched by the sequential addition of $H_2O$ (6 mL), 4M NaOH (6 mL) and $H_2O$ (18 mL). The white slurry thus obtained was filtered through celite and the filter bed was washed with additional $CH_2Cl_2$. The entire filtrate was then concentrated under vacuum to provide crude amine 23.

A mixture of crude 23 was obtained above, nitrophenol 3 g (40 mmol, 8.6 g) and $K_2CO_3$ (60 mmol, 8.3 g) in toluene (80 mL) was refluxed for 3 h. The reaction was then poured into water and extracted with EtOAc. The crude material was purified by flash chromatography (10% MeOH/1% $NH_4OH$/ $CH_2Cl_2$ to provide 24. LCMS: LC retention time 2.16 min.; MS ($ES^+$) 328.1 ($MH^+$).

10% Pd/C (200 mg) and crude 24 obtained above was dissolved in EtOH (50 mL) and the mixture was hydrogenated at atmospheric pressure for 12 h at room temperature. The reaction was filtered through celite and concentrated to provide 25 as a dark oil.

Crude 25 obtained above was dissolved in EtOH (30 mL) and treat with CNBr (22.5 mmol, 2.36 g). The reaction was stirred for 12 h after which it was diluted with 4M NaOH until strongly basic (pH>12) and extracted with $CH_2Cl_2$ (3×). The combined organic layers were washed with brine and dried over $MgSO_4$, then concentrated to provide 26 as a dark oil.

pyrrol-2-ylmethyl)-amine (29i) was prepared according to the procedure described in Example 6 and purified by preparative rpHPLC to provide 25 mg of 29i•3TFA. LCMS: LC retention time 1.32 min.; MS ($ES^+$) 397.2 ($MH^+$).

Example 7

$C_5$ aminomethl-2-aminobenzimidazoles—Reductive Amination

Example 7

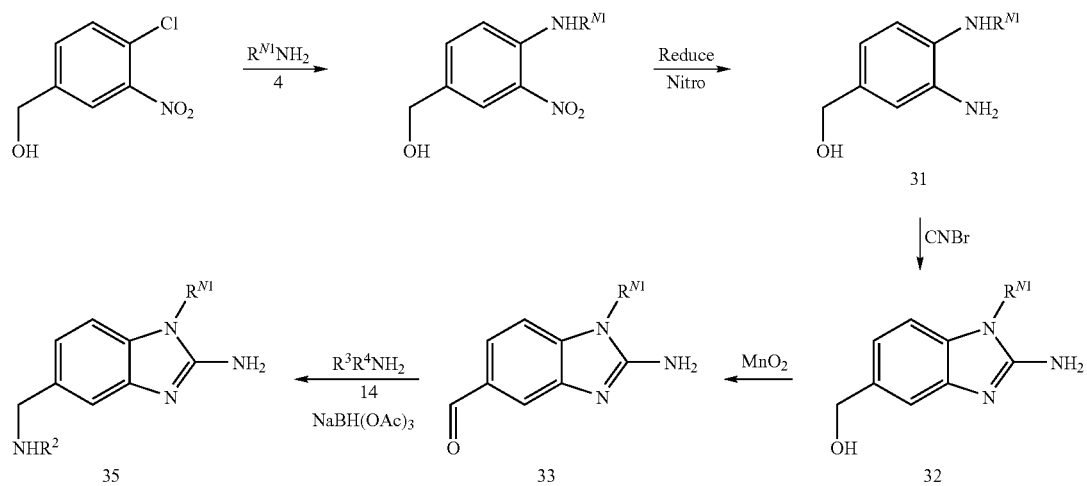

The crude residue was purified by flash column chromatography on neutral alumina (5-10% $MeOH/1\%$ $NH_4OH/CH_2Cl_2$) to provide 26 (0.94 g) as a dark oil. LCMS: LC retention time 0.507 min.; MS ($ES^+$) 323.1 ($MH^+$).

A solution of 26 (2.9 mmol, 0.94 g), DMAP (5 mg) and triethylamine (7.5 mmol, 1.05 mL) in dry $CH_2Cl_2$ (5 mL) was cooled in an ice bath and methanesulfonyl chloride (5.98 mmol, 0.46 mL) was added dropwise over 5 min. The reaction was stirred for 2 h, after which it was diluted with $CH_2Cl_2$ and the organic layer was washed with saturated $Na_2CO_3$, then brine, then dried over $MgSO_4$ and concentrated to provide crude 27. The crude material obtained above was dissolved in DMF (11 mL) and this solution was distributed to 11 vials (1 ML each). $K_2CO_3$ (0.5 mmol, 0.07 g) and the desired primary or secondary amine (0.4 mmol) was added to each reaction vessel. The individual reactions were heated at 60° C. for 14 h, after which the contents of each vessel was diluted with $CH_2Cl_2$ and the organic layer was washed with 4M NaOH, then with brine, and then dried over $MgSO_4$ and concentrated to provide crude 28, which was further purified by preparative reverse phase HPLC.

Dimethyl-{7-[3-(4-pyrrolidin-1-yl-piperidin-1-yl)propoxy]-1,2,3,4-tetrahydrobenzo[4,5]-imidazo[1,2-a]pyrimidin-3-ylmethyl}-amine (28ai) was prepared according to the procedure described in Example 6 and purified by preparative rpHPLC to provide 24 mg of 28ai•3TFA. LCMS: LC retention time 0.59 min.; MS ($ES^+$) 441.2 ($MH^+$).

Heteroaryl or aryl groups (29) could be appended onto the alkyloxy chain at C6 by processing compound 27 per the procedure described in Example 4.

[3-(3-Dimethylaminomethl-1,2,3,4-tetrahydro-benzo[4,5]imidazo[1,2-a]pyrimidin-7-yloxy)-propyl]-methyl-(1H-

A mixture of 3-hydroxymethyl-6-chloronitrobenzene (10.6 mmol, 2 g) and amine 4 (12 mmol) in toluene (10 mL) was refluxed for 2 h. The reaction was then diluted with EtOAc and the organic phase was washed with water and then with brine, then dried over $MgSO_4$ and concentrated to provide 30.

Crude 30 obtained above was reduced and cyclized with CNBr according to the procedure described in Example 1 to provide 32.

A mixture of 32 (2.5 mmol, 0.63 g) and $MnO_2$ (10 mmol, 0.87 g) in $CH_2Cl_2$ was refluxed for 6 h. The reaction was filtered through celite and concentrated to provide 33, which was purified by chromatography on neutral alumina (5% $MeOH/CH_2Cl_2$).

A mixture of aldehyde 33 (0.3 mmol, 0.075 g), 3-dimethylaminopropylamine (0.9 mmol, 0.15 mL), glacial acetic acid (1 drop) and $NaBH(OAc)_3$ (0.45 mol, 0.1 g) in $CH_2Cl_2$ (2 mL) was stirred overnight. The reaction was diluted with $CH_2Cl_2$ and the organic phase was washed with water, then with brine, then dried over $MgSO_4$ and then concentrated to provide 35, which was purified by rpHPLC.

1-(3-Dimethylamino-propyl)-5-morpholin-4-ylmethyl-1H-benzoimidazol-2-ylamine (35ra') was prepared according to the procedure described in Example 7 and purified by preparative rpHPLC to provide 29 mg of 35ra'•3TFA. LCMS: LC retention time 0.52 min.; MS ($ES^+$) 318.2 ($MH^+$).

1-(3-Dimethylamino-propyl)-5-(3-dimethylaminopropyl)-aminomethyl-1H-benzoimidazol-2-ylamine (35qa') was prepared according to the procedure described in Example 7 and purified by preparative rpHPLC to provide 32 mg of 35aqa'•3TFA. LCMS: LC retention time 0.41 min.; MS ($ES^+$) 333.2 ($MH^+$).

Example 8

Alkylation of 2-aminobenzimidazole

Example 8

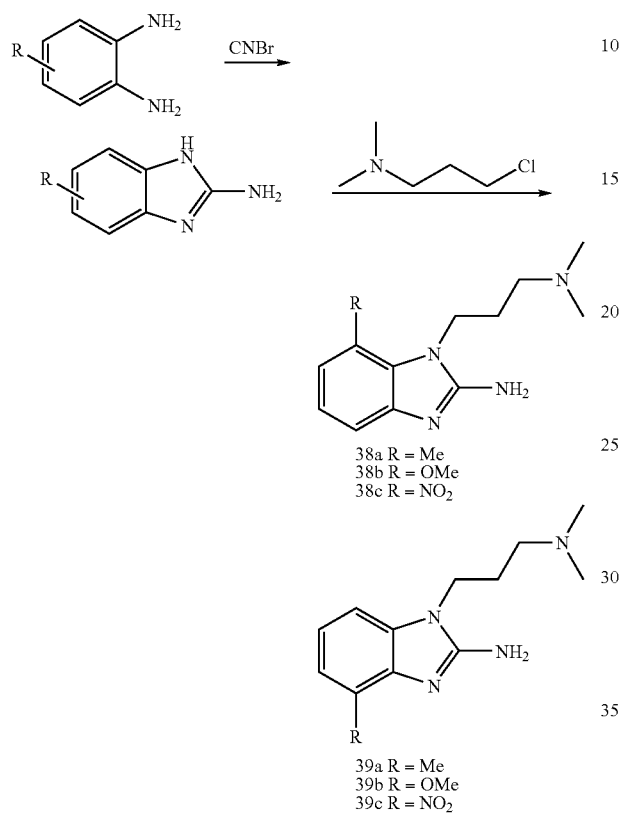

38a R = Me
38b R = OMe
38c R = NO$_2$

39a R = Me
39b R = OMe
39c R = NO$_2$

A mixture of 2,3-dinitrophenol (5.43 mmol, 1 g), iodomethane (21.7 mmol, 1.35 mL) and K$_2$CO$_3$ (21.7 mmol, 2.99 g) was stirred at room temperature for 14 h. The reaction was then filtered through celite and the filter bed was washed with additional acetone. The filtrate was concentrated to provide 2,3-dinitroanisole (100%), which was dissolved in a mixture of EtOH/H$_2$O (1:1, 20 mL) and Fe (19.4 mmol, 1.06 g) and concentrated HCl (8 drops) was added. The mixture was refluxed for 90 min., after which it was filtered through celite and the filter bed was washed with additional EtOH. The filtrate was concentrated and basified (pH>12) with 4 M NaOH and the aqueous layer was extracted with CH$_2$Cl$_2$. The organic phase was then separated and washed with brine, dried MgSO$_4$ and concentrated to provide 2,3-diaminoanisole 36b (0.65 g).

Cyanogen bromide (7.05 mmol, 0.74 g) was added to a solution of 2,3-diaminoanisole (4.7 mmol, 0.65 g) in EtOH (10 mL) and the reaction was stirred at room temperature for 14 h. The reaction was diluted with H$_2$O and then basified (pH>12) using 4 M NaOH. The aqueous layer was extracted with CH$_2$Cl$_2$. The organic phase was then separated and washed with brine and then dried over MgSO$_4$ and then concentrated to provide 2-aminobenzimidazole 37b.

A mixture of crude 37 obtained above, KOH (4 mmol, 0.224 g) and dimethylaminopropyl chloride. HCl (2 mmol, 0.32 g) was refluxed in EtOH (5 mL) for 14 h. The reaction was diluted with CH$_2$Cl$_2$ and the organic phase was washed with water and then with brine and then dried over MgSO$_4$ and then concentrated to provide a mixture of 38b and 39b, which was separated by preparative rpHPLC.

1-(3-Dimethylamino-propyl)-4-methoxy-1H-benzoimidazol-2-ylamine (38b) and 1-(3-Dimethylamino-propyl)-4-methoxy-1H-benzoimidazol-2-ylamine (39b) were purified by preparative rpHPLC to provide 38b'•2TFA (8 mg) and 39b•3TFA (29.5 mg). 38b LCMS: LC retention time 1.36 min.; MS (ES$^+$) 249.1 (MH$^+$). 39b LCMS: LC retention time 1.46 min.; MS (ES$^+$) 249.1 (MH$^+$).

The nitro-substituted 2-aminobenzimidazoles 38c and 39c could be reduced to the corresponding diaminobenzimidazoles using 10% Pd/C and hydrogen gas.

Example 9

Synthesis of 2-aminobenzimidazoles

Example 9

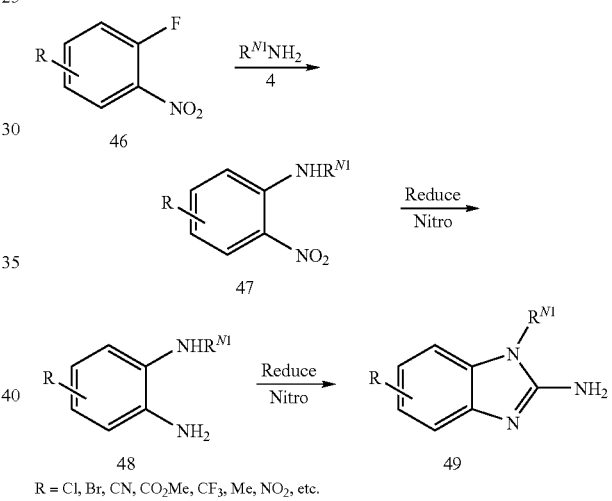

R = Cl, Br, CN, CO$_2$Me, CF$_3$, Me, NO$_2$, etc.

Amine 4 (2.4 mmol was added to a mixture of fluoronitro compound 46 (2 mmol) and CaCO$_3$ (0.4 g, 4 mmol) in CH$_2$Cl$_2$ (2 mL) at room temperature. The reaction was stirred for 12 h, after which it was filtered through celite and the filter pad was washed with additional CH$_2$Cl$_2$. The solvent was removed by concentration and the crude product was hydrogenated using 10% Pd/C (50 mg) and H$_2$ gas (Balloon) in EtOH (10 mL) for 12 h at room temperature, after which the reaction was filtered through celite and concentrated. The crude product thus obtained was suspended in water (2 mL) and treated with CNBr (4 mmol, 0.41 g) and the reaction was stirred for 12 h at room temperature. The reaction was basified using 4M NaOH (pH>12) and the aqueous layer was extracted with CH$_2$Cl$_2$. The layers were separated and the organic layer was dried MgSO$_4$ and concentrated. The material thus obtained was washed with ether (24 mL) and dried under high vacuum to provide the 2-aminobenzimidazole 49.

When the R group is nitro, the 2-aminobenzimidazole 49 can be reduced to the corresponding diamino-benzimidazole using 10% Pd/C (catalytic amount) and hydrogen gas at atmospheric pressure. Filtering the reaction through celite followed by solvent removal under vacuum provides the final diaminobenzimidazole in essentially quantitative yield.

1-(3-Dimethylaminopropyl)-5-trifluoromethyl-1H-benzoimidazol-2-ylamine (49d) was prepared by procedure described in Example 9. $^1$H NMR (200 MHz, CDCl$_3$) δ 7.62 (1H, s), 7.29 (1H, d, J=8.3), 7.09 (1H, d, J=8.4), 6.44 (2H, s, br), 4.05 (2H, m), 2.26 (3H, s), 2.22 (2H, m), 1.97 (2H, m), 1.97 (2H, m). LCMS: LC retention time 1.57 min.; MS (ES$^+$) 287.1 (MH$^+$).

10% Pd/C (200 mg) and crude 24 obtained above was dissolved in EtOH (50 mL) and the mixture was hydrogenated at atmospheric pressure for 12 h at room temperature. The reaction was filtered through celite and concentrated to provide 25 as a dark oil.

Dimethyl-{7-[3-(4-pyrrolidin-1-ylpiperidin-1-yl)propoxy]-1,2,3,4-tetrahydro-benzo[4,5]imidazo[1,2-a]pyrimidine-3-ylmethyl}-amine (28ai) was prepared according to the procedure described in Example 10 and purified by preparative reverse phase HPLC to provide 25 mg of 29i•3TFA. LCMS: LC retention time 1.32 min.; MS (ES$^+$) 397.2 (MH$^+$).

When the R group is nitro, the 2-aminobenzimidazole 49 can be reduced to the corresponding diaminobenzimidazole using 10% Pd/C (catalytic amount) and hydrogen gas at atmospheric pressure. Filtering the reaction through celite followed by solvent removal under vacuum provides the final diaminobenzimidazole in essentially quantitative yield.

(1-(3-Dimethylamino-propyl)-5-trifluoromethyl-1H-benzoimidazol-2-ylamine (49d) was prepared by procedure described in Example 9. $^1$H NMR (200 MHz, CDCl$_3$) δ 7.62 (1H, s), 7.29 (1H, J=8.3), 7.09 (1H, J=8.4), 6.44 (2H, s, br), 4.05 (2H, m), 2.26 (3H, s), 2.22 (2H, m), 1.97 (2H, m), 1.97 (2H, m). LCMS: LC retention time 1.57 min.; MS (ES$^+$) 287.1 (MH$^+$).

Example 10

Synthesis of 6-alkylaminoalkyl-2-aminobenzimidazoles

Amine 4 (16.7 mmol) was added to mixture of 4-bromo-2-fluoronitrobenzene (11.18 mmol, 2.45 g) and CaCO$_3$ (0.4 g, 4 mmol) in CH$_2$Cl$_2$ (2 mL) at rt. The reaction was stirred for 12 h, after which it was filtered through celite and the filter pad washed with additional CH$_2$Cl$_2$. The filtrate was then washed with water, then brine, then dried over MgSO$_4$ and concentrated to provide 51.

A mixture of 51 (3.67 mmol, 1 g), copper iodide (0.183 mmol, 0.034 g), Pd(Ph$_3$)$_3$ (0.09 mmol, 0.103 g) and triethylamine (14.68 mmol, 2 mL) in dry THF (36 mL) was cooled in an ice bath. Alkyne 52 (5.5 mmol, 0.63 mL) was added to the reaction and the mixture was stirred at room temperature for 14 h. The solvent was the removed under vacuum and the residue was dissolved in CH$_2$Cl$_2$ and the organic phase was washed with water, then brine, and then dried and concentrated to provide 53.

10% Pd/C (100 mg) and crude 53 obtained above was dissolved in EtOH (20 mL) and the mixture was hydrogenated at atmospheric pressure for 12 h at room temperature. The reaction was filtered through celite and concentrated to provide 54 as a dark oil.

Crude 6 obtained above was dissolved in EtOH (8 mL) and treated with CNBr (4.9 mmol, 0.52 g). The reaction was stirred for 12 h, after which it was diluted with 4 M NaOH until strongly basic (pH>12) and extracted with CH$_2$Cl$_2$ (3×). The combined organic layers were washed with brine, dried MgSO$_4$ and concentrated to provide 55 as a dark oil, which was purified by preparative rpHPLC.

1,6-Bis-3-dimethylamino-propyl)-1H-benzoimidazole-2-ylamine (55a') was prepared according to the procedure described in Example 10 and purified by preparative reverse phase HPLC to provide mg of 55a'•3TFA. LCMS: LC retention time 0.57 min.; MS (ES$^+$) 352.1 (MH$^+$).

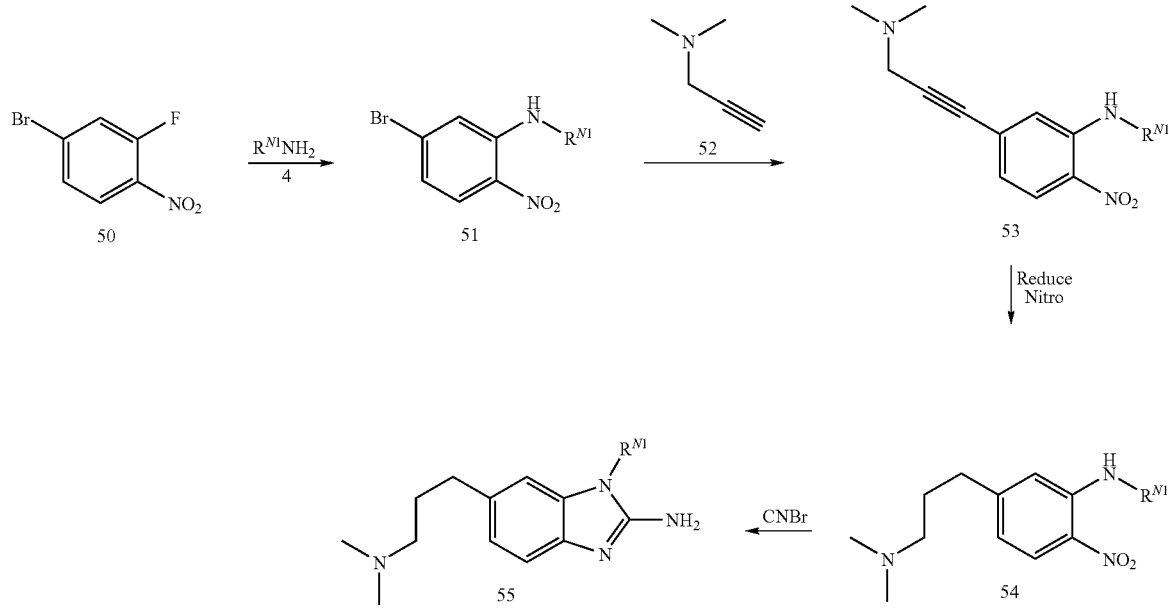

Example 11
Synthesis of 6-alkylaminoalkylthio-2-aminobenzimidizole
Example 11
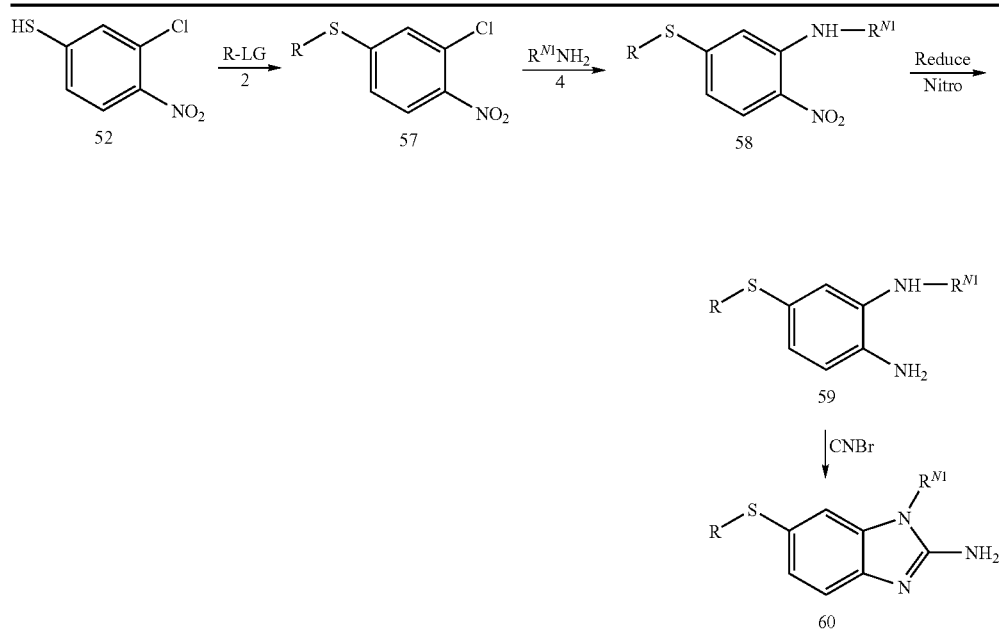
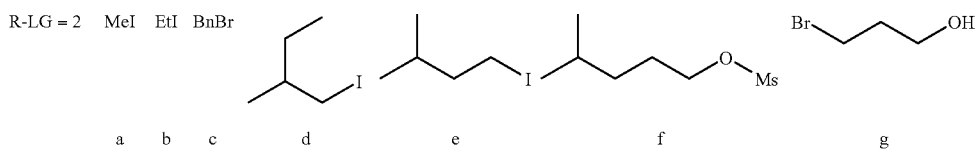
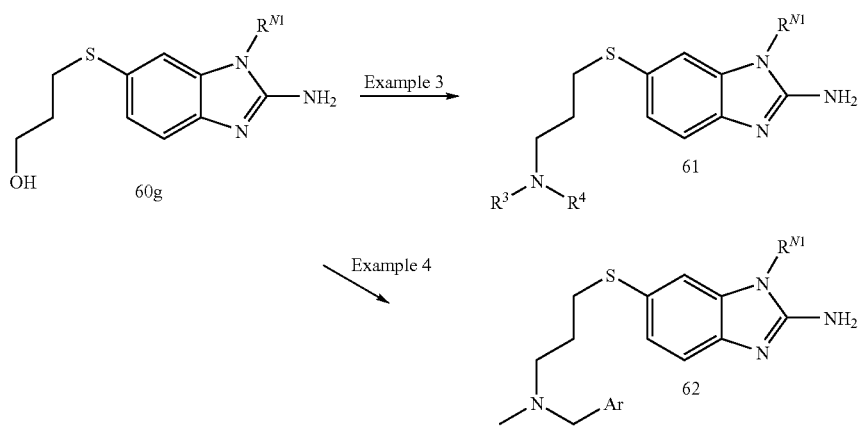
2-amionbenzimidazole 60 is prepared starting from 3-chloro-4-nitrothiophenol according to the procedure described in Example 1. 2-aminobenzimidazoles 61 and 62 are prepared starting from 60 g according to the procedure described in Example 3 and Example 4 respectively.

Example 12

Synthesis of C6-C7 Constrained 2-amionbenzimidazoles

Example 12

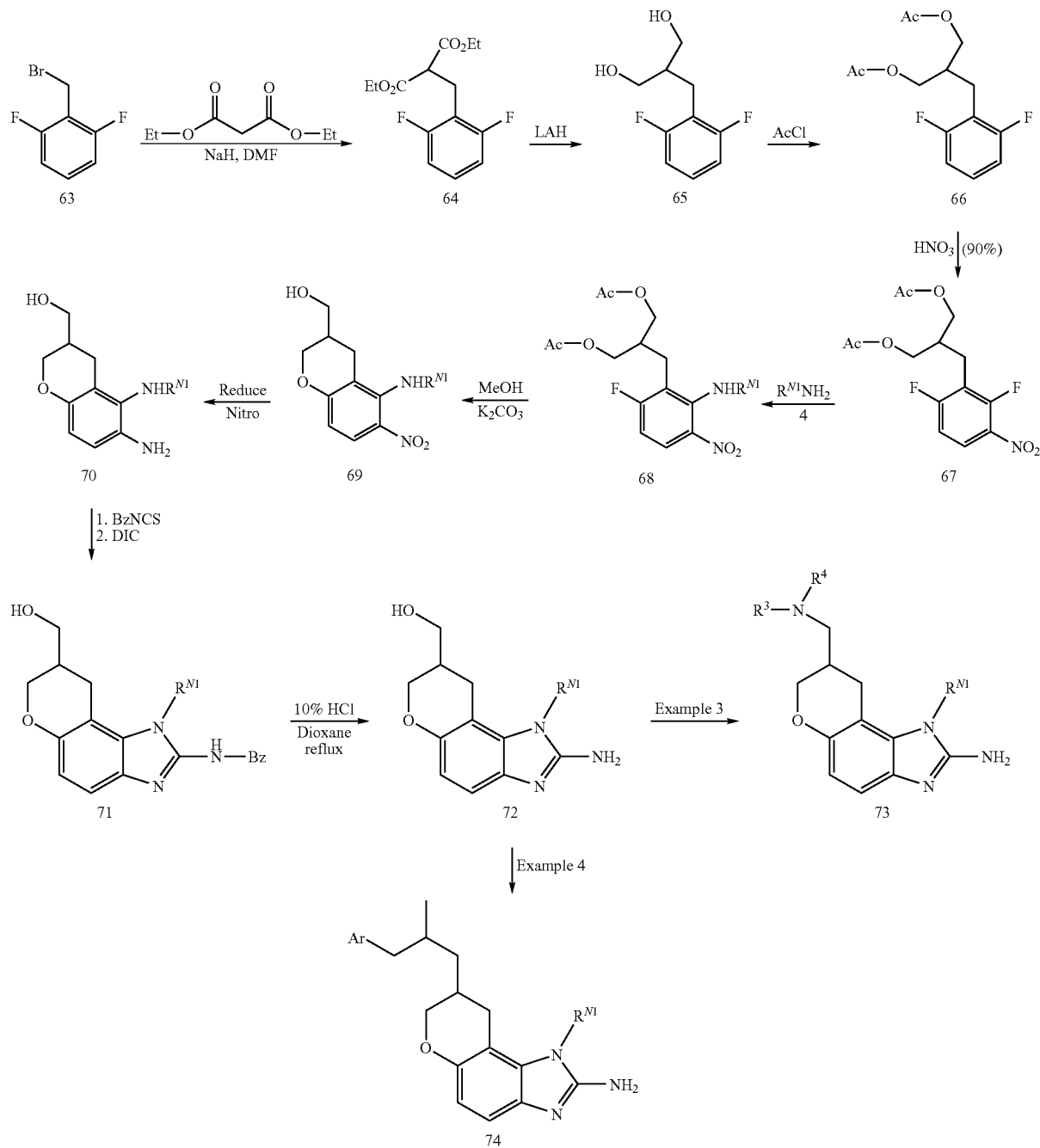

Diethylmalonate (40 mmol, 6.1 mL) was added to a suspension of NaH (44 mmol, 1.76 g of a 60% dispersion in mineral oil) in dry THF (60 mL). After stirring for 10 min. at room temperature, the suspension turned to a clear solution (with evolution of hydrogen), which was then cooled to −78° C. Bromide 63 (40 mmol, 8.26 g) in dry THF (20 mL) was then added dropwise over 20 minutes to the reaction. The ice bath was removed and the reaction was gradually allowed to warm up to room temperature over 2-3 h. The reaction was then diluted with $CH_2Cl_2$, extracted with water (2×) and the organic phase was washed with brine, dried over MgSO$_4$ and concentrated to provide 64, which was used without any further purification.

Crude 64 obtained above in dry THF (60 mL) was added dropwise to a cold (−78° C.) suspension of LAH (4.48 g) in THF (300 mL). The reaction was gradually allowed to warm to room temperature over 14 h, after which it was recooled in an ice bath. Water (4.5 mL) was carefully added to the reaction, followed by sequential addition of 4M NaOH (4.5 ml) and water (13.5 mL). The reaction was further diluted with ether (100 mL), filtered through celite and the filter bed was thoroughly washed with additional ether. The filtrate was concentrated and the residue was purified by column chromatography to provide 65 (50% over two steps). $^1$H NMR (300 MHz, CDCl$_3$) δ 7.16 (m, 1H), 6.85 (m, 2H), 3.8 (m, 4H), 2.7 (d, 2H), 2.0 (m, 1H).

A solution of acetyl chloride (59 mmol, 4.21 mL) in dry CH$_2$Cl$_2$ (60 mL) was added dropwise to a cold (0° C.) solution of diol 65 (25.6 mmol, 5.18 g), triethylamine (64 mmol, 8.9 mL) and DMAP (2.56 mmol, 0.32 g) in dry CH$_2$Cl$_2$ (190 mL). The reaction was then stirred for an additional 14 h at room temperature, after which it was diluted with CH$_2$Cl$_2$ and the organic phase was washed with 5% HCl, then with brine, then dried over MgSO$_4$ and concentrated to provide 66, which was used without any further purification. $^1$H NMR (300 NMR, CDCl$_3$) δ 7.16 (m, 1H), 6.85 (m, 2H), 4.0 (d, 4H), 2.78 (d, 2H), 2.37 (m, 1H), 2.02 (s, 6H).

Crude 66 (25.8 mmol, 7.38 g) obtained above was cooled in an ice bath and fuming nitric acid (15 mL) was added over 5 min. The reaction was stirred for 1 h in the ice bath, after which it was diluted with ice water. The cold aqueous solution was then extracted with CH$_2$Cl$_2$ (3×) and the combined organic phases were washed with brine, then dried over MgSO$_4$ and concentrated to provide 67, which was used without any further purification. $^1$H NMR (300 NMR, CDCl$_3$) δ: 8.0 (m, 1H), 7.0 (m, 2H), 4.06 (d, 4H), 2.85 (d, 2H), 2.4 (m, 1H), 2.02 (s, 6H).

Amine 4 (30 mmol) was added to a suspension of crude 67 (20 mmol) and CaCO$_3$ (28 mmol, 2.8 g) in CH$_2$Cl$_2$ (40 mL). The reaction was stirred for 14 h at room temperature, after which it was diluted with CH$_2$Cl$_2$ and the organic phase was washed with water, then with brine, then dried over MgSO$_4$ and concentrated to provide nitroaniline 68, which was used without any further purification.

A suspension of crude nitroaniline 68 (18.4 mmol) obtained above and K$_2$CO$_3$ (54 mmol, 7.46 g) in MeOH (180 mL) was stirred at room temperature for 72 h and 40° C. for 24 h. The solvent was then removed by concentration under reduced pressure and the residue was dissolved in water an the aqueous solution was extracted with CH$_2$Cl$_2$ (3×). The combined organic layers were then washed with brine, then dried over MgSO$_4$ and concentrated to provide crude 69, which was used without any further purification.

A solution of crude 69 in EtOH (200 mL) was treated with 1% Pd/C (0.46 g) and the mixture was hydrogenated at atmospheric pressure for 20 h to provide crude 70, which was used without any further purification.

Benzoylisothiocyanate (9.76 mmol, 1.31 mL) was added to a cold (0° C.) solution of crude 70 in CH$_2$Cl$_2$ (20 mL) and the mixture was stirred for an additional 2 h at room temperature. Diisopropylethylamine (29.28 mmol, 5.1 mL) was then added to the reaction, followed by diisopropylcarbodiimide (14.64 mmol, 2.3 mL) and the whole was then stirred at room temperature for 14 h. The reaction was diluted with CH$_2$Cl$_2$ and the organic phase was washed with water. The CH$_2$Cl$_2$ layer was then extracted with 5% HCl (2×) and the acidic aqueous layers were combined and washed with EtOAc (1X).

The acidic aqueous layer was then basified with solid NaOH until strongly basic (pH>12) and extracted with CH$_2$Cl$_2$ (3×). The combined organics were further washed with brine, dried over MgSO$_4$ and concentrated to provide 71, which was used without any further purification.

Crude 71 (1.62 g, 4 mmol) was dissolved in a mixture of 1,4-dioxane (2.4 mL) and 10% HCL (5.6 mL) and the reaction was refluxed for 14 h. The reaction was then cooled and basified with solid NaOH until strongly basic (pH>12) and the aqueous layer was extracted with CH$_2$Cl$_2$ (3×). The combined organic layers were then washed with brine, dried over MgSO$_4$ and concentrated to provide 72.

8-Dimethylaminomethyl-1-(3-dimethylamino-propyl)-1, 7,8,9-tetrahydro-chromeno[5,6-d]imidazol-2-ylamine (73a') was prepared from 72a' according to the procedure described in Example 3, using dimethylamine (excess) as the nucleophile for mesylate displacement and purified by preparative rpHPLC to provide 73a'•CH$_3$CO$_2$H (44.4 mg). LCMS: LC retention time 0.34 min.; MS (ES$^+$) 332.2 (MH$^+$).

1-(3-Dimethylaminopropyl)-8-{[methyl-(1-methyl-1H-pyrrol-2-ylmethyl)-amino]-methyl}-1,7,8,9-tetrahydro-chromeneo[5,6-d]imidazol-2-ylamine (74a') was prepared from 72a' according to the procedure described in Example 4 and purified by preparative rpHPLC to provide 74a'•CH$_3$CO$_2$H (21.1 mg). LCMS: LC retention time 0.51 min.; MS (ES$^+$) 411.2 (MH$^+$).

Example 13

Synthesis of Extended Tether C$_6$-C$_7$ Constrained 2-aminobenzimidazoles

Methanesulfonyl chloride (1.79 mmol, 0.14 mL) was added dropwise to a cold solution (0° C.) of 2-aminobenzimidazole 72 (1.19 mmol, 0.36 g, prepared according to Example 12), triethylamine (1.79 mmol, 0.25 mL) and dimethylaminopyridine (10 mg) in dry CH$_2$Cl$_2$ (2 mL). The reaction was stirred for 2 h, after which it was diluted with CH$_2$Cl$_2$ and the organic phase was extracted with water, then with brine, then dried over MgSO$_4$ and concentrated to provide crude mesylate mixture 75 and 76.

The crude material obtained above was dissolved in DMF (1 mL) and KCN (68 mg) was added and the reaction was heated for 14 h at 60° C. The reaction was then cooled and diluted with water and extracted with CH$_2$Cl$_2$ to provide the corresponding cyanide 77.

The crude 77 obtained above was dissolved in a mixture of MeOH (0.8 mL) and strong NH$_3$ solution (0.2 mL) and treated with Raney Nickel catalyst. The whole mixture was then hydrogenated to provide amine 78, which was isolated by filtration through celite.

8-(2-Aminoethl)-1-(3-dimethylaminopropyl)-1,7,8,9-tetrahydrochromeno[5,6-d]imidazole-2-ylamine (78a') was prepared using the procedure described in Example 34 and purified by preparative rpHPLC to provide 78a' •CH$_3$CO$_2$H (12.6 mg). LCMS: LC retention time 0.41 min.; MS (ES$^+$) 318.2 (MH$^+$).

In the study design, 3-4 female mice/group were dosed with 0, 5 or 45 mg/kg of IBIS00553642, IBIS000408094, or IBIS00405746 for 3 days (i.p.). Clinical signs, body weights, clinical pathology, organ weights, and histopathology endpoints were evaluated.

Example 13

Synthesis of Extended Tether C6-C7 Constrained 2-aminobenzimidazoles

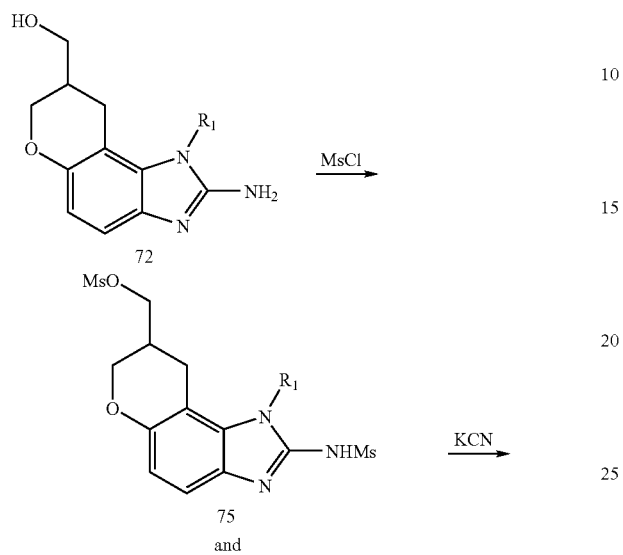

Methanesulfonyl chloride (1.79 mmol, 0.14 mL) was added dropwise to a cold solution (0° C.) of 2-aminobenzimidazole 72 (1.19 mmol, 0.36 g, prepared according to example 12), triethylamine (1.79 mmol, 0.25 mL) and dimethylaminopyridine (10 mg) in dry $CH_2Cl_2$ (2 mL). The reaction was stirred for 2 hours after which it was diluted with $CH_2Cl_2$ and the organic phase was extracted with water, brine, dried (MgSO4) and concentrated to provide crude mesylate mixture 75 and 76.

The crude material obtained above was dissolved in DMF (1 mL) and KCN (68 mg) was added and the reaction was heated for 14 h at 60° C. The reaction was then cooled and diluted with water and extracted with $CH_2Cl_2$ to provide the corresponding cyanide 77.

The crude cyanide 77 obtained above, was dissolved in a mixture of MeOH (0.8 mL) and strong $NH_3$ solution (0.2 mL) and treated with Raney Nickel catalyst. The whole mixture was then hydrogenated to provide amine 78, which was isolated by filtration through celite.

8-(2-Amino-ethyl)-1-(3-dimethylamino-propyl)-1,7,8,9-tetrahydro-chromeno[5,6-d]imidazol-2-ylamine (78a') was prepared using the procedure described in example 13 and purified by reverse phase preparative HPLC to provide 78a'·3$CH_3CO_2H$ (12.6 mg). LCMS: LC retention time 0.41 min.; MS (ES$^+$) 318.2 (MH$^+$).

Example 14

Synthesis of C6-C7 Constrained 2-aminobenzimidazoles (Benzofuran Series)

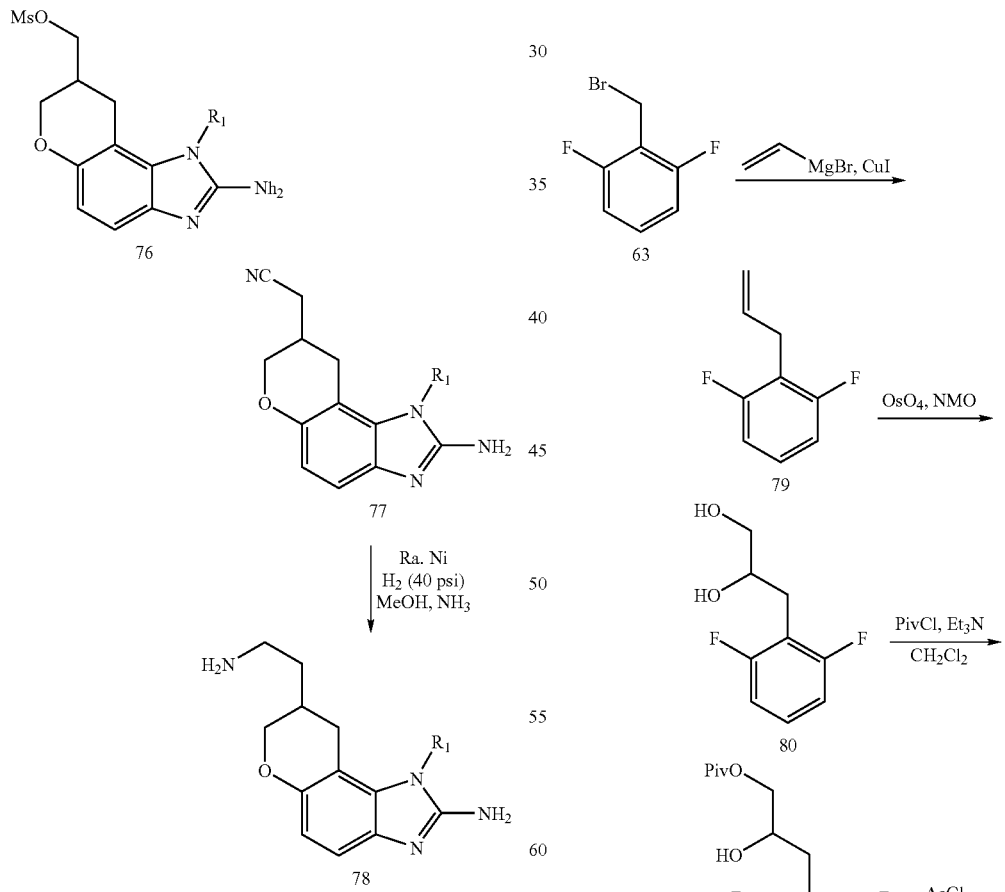

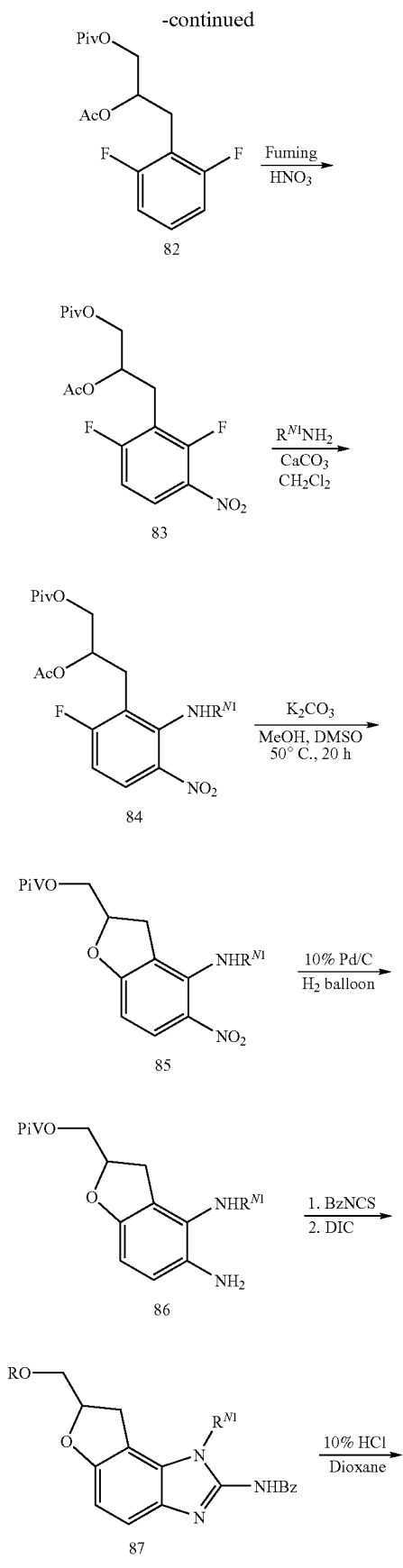

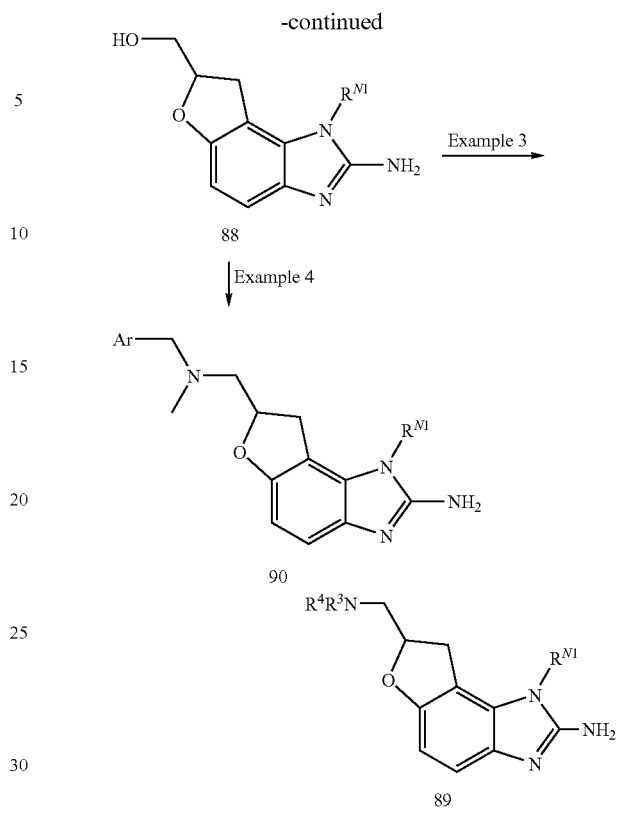

Vinyl Magnesium Bromide (22.5 ml of a 1M solution in THF, 22.5 mmol) was slowly added to a cold (0° C.), stirred suspension of CuI (1.5 mmol, 0.285 g) and 2,2'-dipyridyl (1.5 mmol, 0.234 g) in dry THF (40 mL). After stirring for 30 min, the reaction was cooled to −78° C. and bromide 63 was added dropwise as a solution in dry THF (10 mL). The reaction mixture was allowed to warm gradually over 3 h after which it was quenched with sat. NH$_4$Cl solution. The reaction was then diluted with EtOAc and the aqueous phase was separated. The organic phase was then washed with additional sat. NH$_4$Cl, brine, dried (MgSO$_4$) and concentrated to provide crude 79, which was used without any further purification.

Crude 79 obtained above was dissolved in acetone (50 mL) and the reaction mixture was treated with OsO$_4$ (catalytic) and N-methylmorpholine-N-oxide (1.5 g). After stirring for 14 h at rt, the reaction was evaporated to dryness and purified by column chromatography (silica gel, eluting with 10% EtOAc–50% EtOAc in hexanes) to provide diol 80 (1.35 g) as a white solid.

Trimethylacetyl chloride (5.2 mmol, 0.64 mL) was added dropwise to a cold (0° C.), stirred solution of diol 80 (3.47 mmol, 0.66 g), Et$_3$N (5.2 mmol, 0.73 mL) and catalytic DMAP in dry CH$_2$Cl$_2$ (5 mL). After stirring at rt for 14 h the reaction was diluted with CH$_2$Cl$_2$ and extracted with 5% HCl, sat. NaHCO$_3$, brine, dried (MgSO$_4$) and concentrated to provide pivaloate ester 81, which was used without any further purification.

Acetyl chloride (17 mmol, 1.15 mL) was added dropwise to a cold (0° C.), stirred suspension of pivaloate 81 (3.47 mmol) and K$_2$CO$_3$ (17.3 mmol, 2.39 g) in dry CH$_2$Cl$_2$ (5 mL). After stirring for 2 h, the reaction was diluted with CH$_2$Cl$_2$, filtered (to remove K$_2$CO$_3$) and the organic layer was washed with water, dried (MgSO$_4$) and concentrated to provide crude 82, which was used without any further purification.

Crude 82 (3.47 mmol) obtained above was cooled in an ice bath and fuming nitric acid (1 mL) was added over 5 min. After stirring at 0° C. for 1 h, the reaction was diluted with water and extracted with $CH_2Cl_2$. The organic layer was separated and washed with brine, dried ($MgSO_4$) and concentrated to provide crude 83, which was used without any further purification.

Amine 4 (4.9 mmol) was added to a suspension of crude 83 (3.27 mmol) and $CaCO_3$ (3.5 mmol, 0.35 g) in $CH_2Cl_2$ (6 mL). The reaction was stirred for 14 h at rt after which it was diluted with $CH_2Cl_2$ and the organic phase was washed with $H_2O$, brine, dried ($MgSO_4$) and concentrated to provide nitroaniline 84 which was used without any further purification.

A suspension of crude nitroaniline 84 (3.27 mmol) obtained above, $K_2CO_3$ (12.8 mmol, 1.74 g), MeOH (0.75 mL) in dry DMSO (30 mL) was stirred at rt for 2 h and 50° C. for 20 h. The solvent was then removed by concentration under reduced pressure and the residue was dissolved in $H_2O$ and the aq. solution was extracted with $CH_2Cl_2$ (3×). The combined organic layers were then washed with brine, dried ($MgSO_4$) and concentrated to provide crude 85, which was used without any further purification.

A solution of crude 85 in EtOH (50 mL) was treated with 10% Pd/C (0.1 g) and the mixture was hydrogenated at atmospheric pressure for 20 h to provide crude 86 which was used without any further purification.

Benzoylisothiocyanate (3.3 mmol, 0.44 mL) was added to a cold (0° C.) solution of crude 86 in $CH_2Cl_2$ (15 mL) and the mixture was stirred for an additional 2 h at rt. Diisopropylethylamine (13.2 mmol, 2.29 mL) was then added to the reaction followed by Diisopropylcarbodimide (4.6 mmol, 0.72 mL) and the reaction mixture was stirred at rt for 14 h. The reaction was diluted with $CH_2Cl_2$ and the organic phase was washed with $H_2O$. The $CH_2Cl_2$ layer was then extracted with 5% HCl (2×) and the acidic aqueous layers were combined and washed with EtOAc (1×). The acidic aqueous layer was then basified with solid NaOH till strongly basic (pH>12) and extracted with $CH_2Cl_2$ (3×). The combined organics, were further washed with brine, dried ($MgSO_4$) and concentrated to provide 87, which was used without any further purification.

A mixture of crude 87 (3 mmol), 1,4-dioxane (2 mL) and 10% HCl (6 mL) was refluxed for 14 h after which the reaction mixture was cooled and basified with solid NaOH till strongly basic (pH>12). The aqueous layer was extracted with $CH_2Cl_2$ (3×) and the combined organic layers were washed with brine, dried ($MgSO_4$) and concentrated to provide 88.

[2-Amino-1-(3-dimethylamino-propyl)-7,8-dihydro-1H-6-oxa-1,3-diaza-as-indacen-7-yl]-methanol (88a') was prepared according to the general procedure described in example 14 above. Purification by column chromatography on neutral Alumina (eluting with 2-5% MeOH/0.5% $NH_4OH/CH_2Cl_2$) provided 88a' (212 mg). LCMS: LC retention time 0.55 min.; MS (ES+) 291.2 (MH+).

7-Dimethylaminomethyl-1-(3-dimethylamino-propyl)-7,8-dihydro-1H-6-oxa-1,3-diaza-as-indacen-2-ylamine (89a') was prepared from 88a' according to the procedure described in example 3 using dimethylamine (excess) as the nucleophile for mesylate displacement and purified by reverse phase preparative HPLC to provide 89a'. $3CH_3CO_2H$ (86 mg). LCMS: LC retention time 0.40 min.; MS (ES+) 318.2 (MH+).

1-(3-Dimethylamino-propyl)-7-{[methyl-(1-methyl-1H-pyrrol-2-ylmethyl)-amino]-methyl}-7,8-dihydro-1H-6-oxa-1,3-diaza-as-indacen-2-ylamine (90ia') was prepared from 88a' according to the procedure described in example 4 using aldehyde 17i and purified by reverse phase preparative HPLC to provide 90ia'. $3CH_3CO_2H$ (8 mg). LCMS: LC retention time 0.47 min.; MS (ES+) 397.3 (MH+).

Example 15

Synthesis of Double Constrained 2-aminobenzimidazoles (Benzopyran Series)

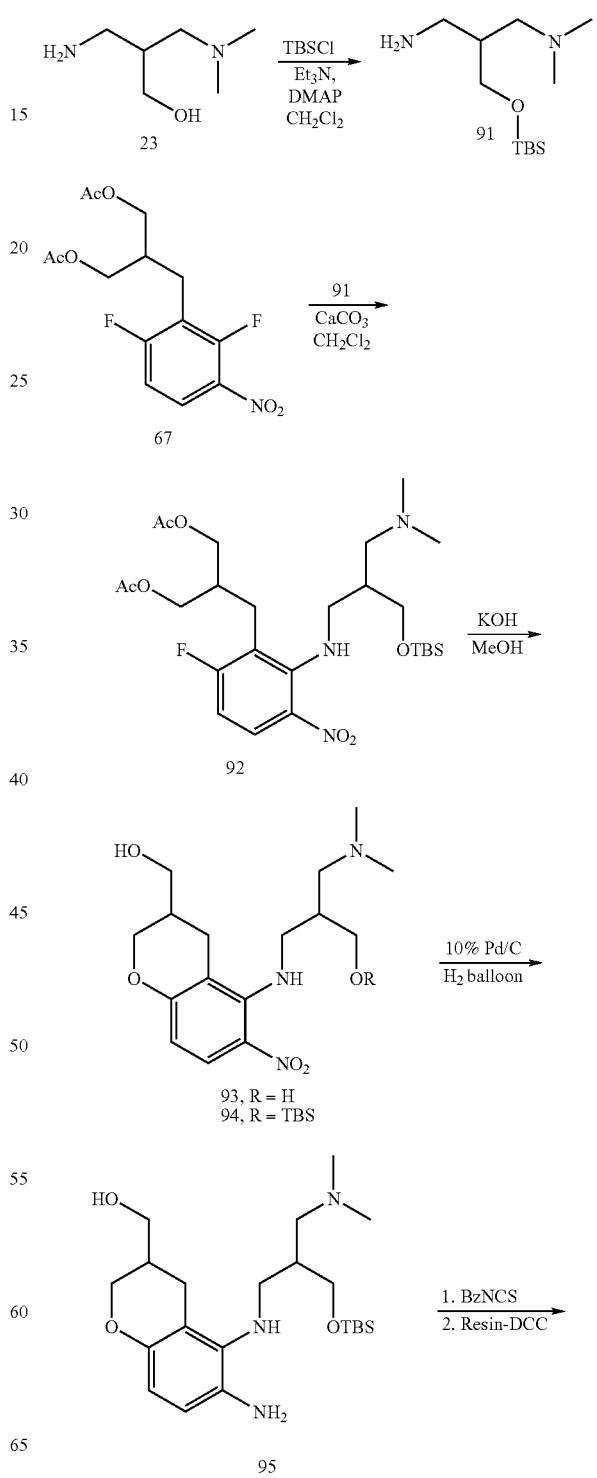

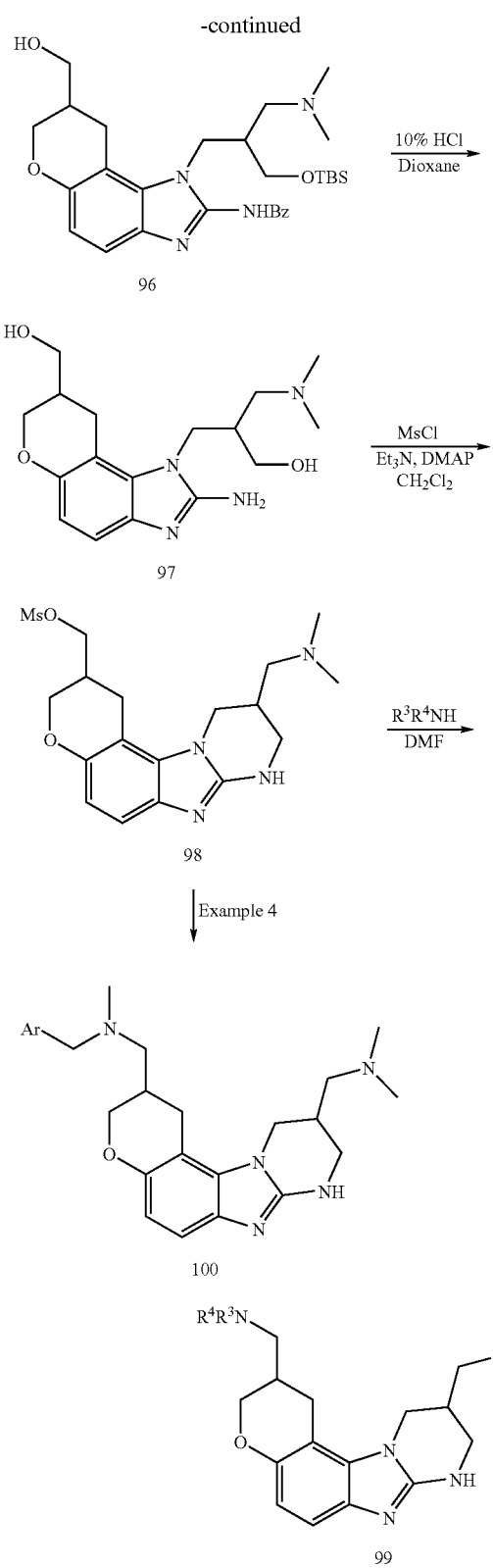

CH₂Cl₂ (20 mL). After stirring at rt for 14 h, the reaction was diluted with CH₂Cl₂ and the organic layer was sequentially washed with water, brine, dried (MgSO₄) and concentrated to provide protected amine 91, which was used without any further purification.

Amine 91 (4 mmol) was added to a suspension of diacetate 67 (4 mmol, 1.32 g) and CaCO₃ (4 mmol, 0.4 g) in CH₂Cl₂ (10 mL). After stirring at rt for 14 h, the reaction was diluted with CH₂Cl₂ and the organic phase was washed with water, brine, dried (MgSO₄) and concentrated to provide crude 92.

A suspension of 92 (5.46 mmol, 3 g) and KOH (32.76 mmol, 1.84 g) in MeOH (55 mL) was stirred at 40° C. for 48 h after which the reaction mixture was evaporated to dryness under vacuum. The reaction was purified by column chromatography to provide 93 (770 mg) and 94 (714 mg).

A solution of 94 (1.58 mmol, 0.71 g) in EtOH (30 mL) was treated with 10% Pd/C (72 mg) and the mixture was hydrogenated at atmospheric pressure for 20 h to provide crude 95 which was used without any further purification.

Benzoylisothiocyanate (1.38 mmol, 0.186 mL) was added drop-wise to a cold (0° C.) solution of 95 (1.38 mmol) in dry CH₂Cl₂ (3 mL). After stirring for 2 h at 0° C., the reaction was treated with diisopropylethylamine (3.1 mmol, 0.5 mL) and polymer supported dicyclohexylcarbodiimide (Resin-DCC, 4.14 mmol, 3.34 g of resin). The reaction was stirred at rt for 14 h after which it was filtered through a sintered glass funnel and the resin was washed with additional CH₂Cl₂. The combined filtrates were collected and evaporated to dryness under vacuum to provide crude 96, which was used without any further purification.

Crude 96 (1.36 mmol, 0.73 g) was refluxed in a mixture of dioxane (0.8 mL) and 10% HCl (1.86 mL) for 8 h after which an additional amount of 10% HCl (1 mL) was added to the reaction mixture. After stirring at rt for an additional 14 h, the reaction was basified with solid sodium hydroxide (ph>12), which resulted in the precipitation of pure 97 that was collected, dried and used without any further purification.

Methanesulfonyl chloride (0.96 mmol, 0.075 mL) was added to a cold (0° C.) solution of 97 (0.34 mmol, 0.117 g), triethylamine (0.96 mmol, 0.13 mL) and DMAP (catalytic) in dry CH₂Cl₂ (1 mL). After stirring for 3 h, the reaction was diluted with CH₂Cl₂ and the organic phase was sequentially washed with sat. Na₂CO₃, brine, dried and concentrated to provide crude 98, which was used without any further purification.

The desired amine (1-5 eq) was added to a solution of crude 98 (0.96 mmol) in DMF (0.2 mL) and the reaction was heated at 40-50° C. for 14 h. The solvent was evaporated under vacuum and the residue was purified by reverse phase preparative HPLC to provide 99.

Benzimidazole 100 is prepared from intermediate 98 by following the general procedure outlined in example 4.

(10-Dimethylaminomethyl-2,3,8,9,10,11-hexahydro-1H-4-oxa-7,8,11a-triaza-benzo[c]-fluoren-2-ylmethyl)-dimethyl-amine (99a') was prepared from 98 according to the procedure described in example 15 using dimethylamine (excess) as the nucleophile for mesylate displacement and purified by reverse phase preparative HPLC to provide 99a'. 3CH₃CO₂H (20 mg). LCMS: LC retention time 0.39 min.; MS (ES⁺) 344.3 (MH⁺).

tert-Butyldimethylsilylchloride (22.08 mmol, 3.33 g) was added to a cold (0° C.) solution of crude amine 23 (18.4 mmol, 2.43 g, prepared according to procedure described in example 6), Et₃N (22.08 mmol, 3.08 mL) and DMAP (catalytic) in dry

Example 16
Synthesis of Double Constrained 2-aminobenzimidazoles (Benzofuran Series)
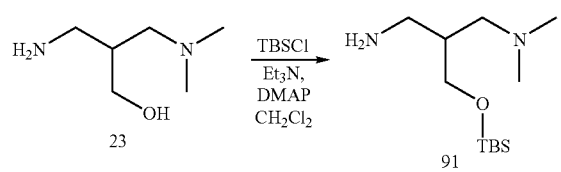
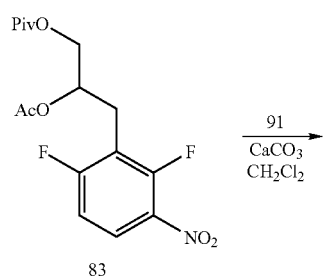
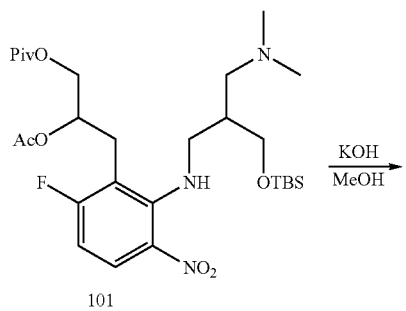
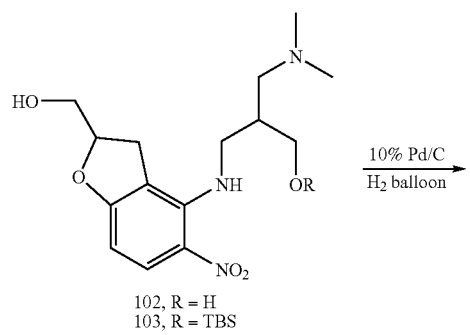
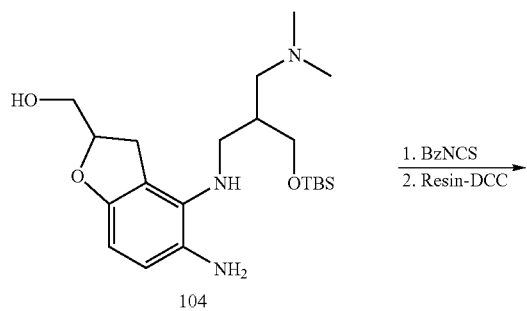
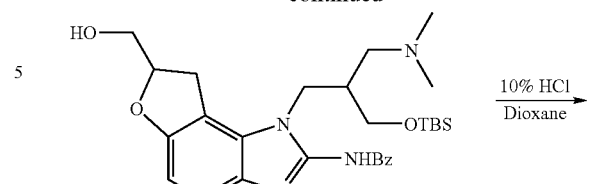
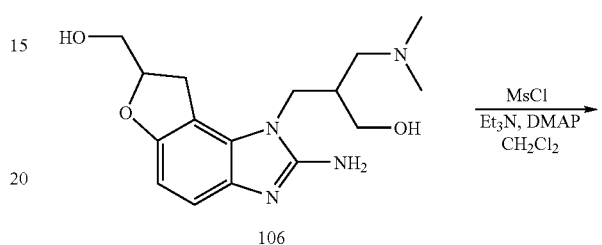
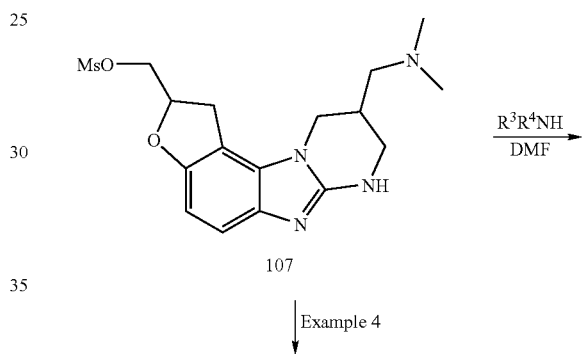
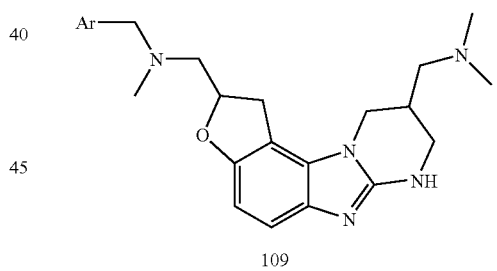
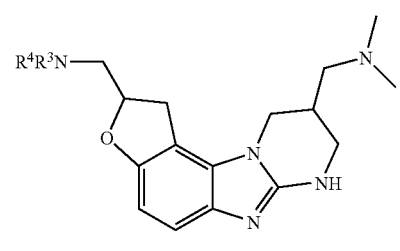
Benzimidazole 108 and 109 are prepared according to the general procedure outlined in example 15 except that pivaloate 83 (example 14) is used as the starting material in place of 67.

Example 17

Synthesis of Enantiomerically Pure Constrained 2-aminobenzimidazoles

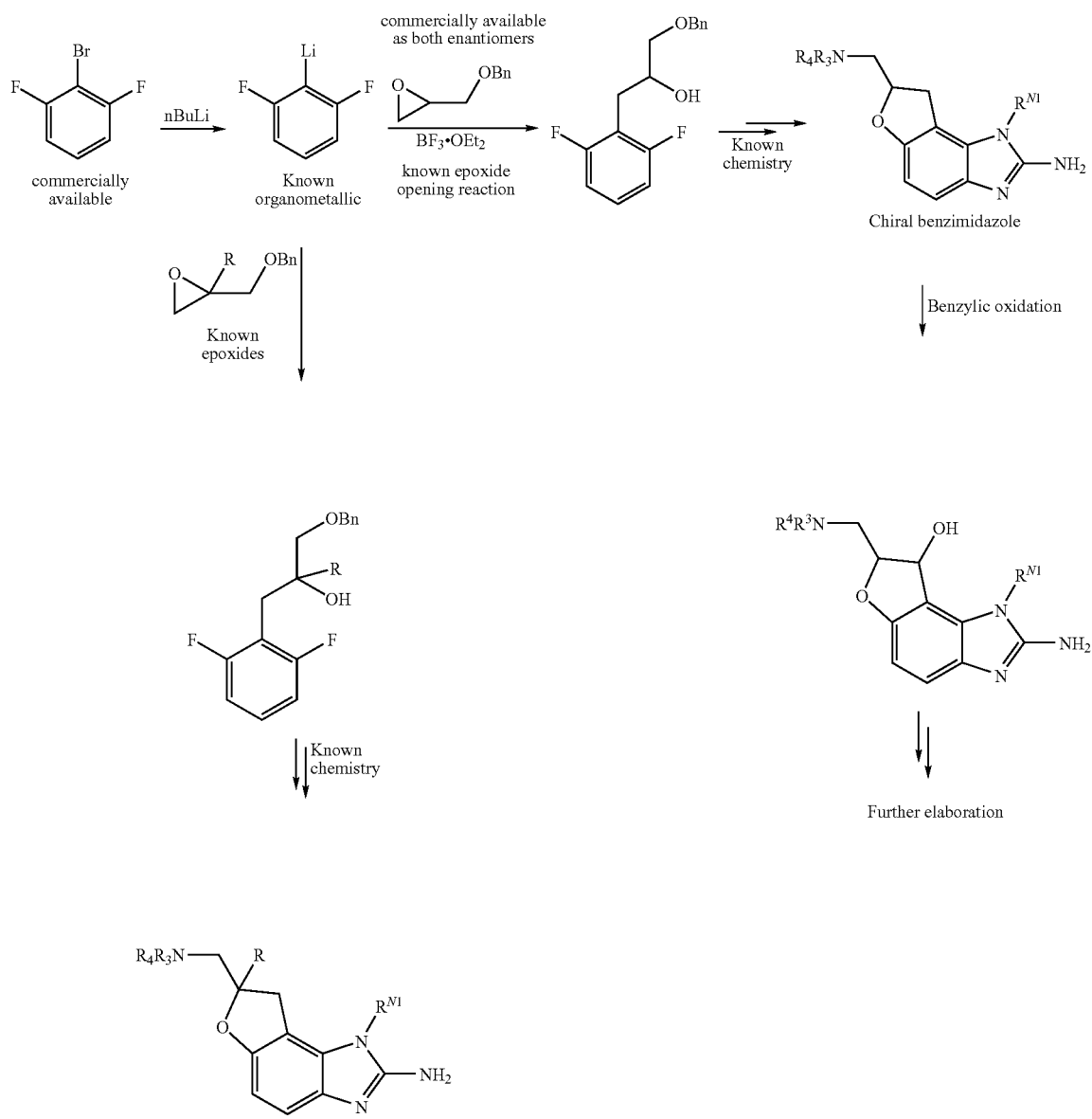

Benzimidazoles consisting of a single enantiomer and/or diastereomer are prepared according to the general procedures used in examples 1-16, except that chirally pure synthons may be substituted for the achiral ones utilized in the previous examples. These synthons are either commercially available, known in the scientific literature, or readily prepared from known materials according to techniques known in the art. As an example, the compounds of examples 14 and 16 can be prepared using an enantiomerically enriched epoxide, which is commercially available. Subsequent elaborations as described in previous examples provide the desired compounds.

Example 18

Mass Spectrometry Based Binding Assay

Screening was performed by measuring the formation of non-covalent complexes between a single ligand or ligand mixture and the appropriate RNA target, along with suitable control structured RNA target(s) simultaneously using a 9.4 T FT-ICR mass spectrometer as detector. Full experimental details of the assay have been described in related literature (Sannes-Lowery, et al. in *TrAC, Trends Anal. Chem.* 2000, 19, 481-491 and Sannes-Lowery, et al. in *Anal. Biochem.* 2000, 280, 264-271. In a typical experiment, 10 μL of an aqueous solution containing 100 mM ammonium acetate buffer, 2.5 or 5 μM of each RNA, and 33% isopropyl alcohol (to aid ion desolvation) was prepared with different concentrations of each ligand or ligand mixture. Samples were introduced into the electrospray ionization source (negative ionization mode) at 1 μL/min and ions were stored for 1 sec in an RF-only hexapole following desolvation. The abundances were integrated from the respective ions for free RNA and the ligand-RNA complex. The primary (1:1 RNA:ligand) and secondary (1:2 complex, if observed). Screening was operated in two modes. In 'HTS' mode, mixtures of 8-12 compounds were screened simultaneously to determine hits, and in 'SAR' mode, $K_D$ values were determined by titrating a single ligand through a concentration range of 0.25-25 μM. The peak ratios were measured at each concentration, then a plot of complex/free RNA versus concentration of ligand added was fitted to a second (or higher) order binding polynomial to determine the $K_D$. For measuring binding to the HCV IRES, RNA subdomains from 20-100 residues were prepared by commercial synthesis which assume the same structure as known in the literature of the HCV IRES and 5-UTR. These subdomains generally include a stable tetraloop (such as GAGA or UUGG), certain stabilizing base pairs (such as substituted GC and CG pairs for weaker pairs), as well as the residues in the natural sequences of HCV isolates. For the stem IIa region, these sequences include, but are not limited to (5' to 3')

(SEQ ID NO.: 1)
CCU GUG AGG AAC UAC UGU CUU CAC GCA GAA AGC GUC

UAG CCA UGG CGU UAG UAU GAG UGU CGU GCA GCC UCC

AGG GGA GGA ACU GCU GGA GAC GCG CAG CCU CC, GGA

GGA ACU ACU GGA GAC GUG CAG CCU CC, GGA GGA ACU

AGC GAG AGC UGC AGC CUC C, and (SEQ ID NO.: 2)
GAG GAA CUA CUG UCU UCA CGC ACC GAG AGG UGA GUG

UCG UGC AGC CUC.

More particular presentation of the stem region IIa of the 5'-UTR of HCV RNA can be more fully understood according to the following literature references: Kieft, J. S.; Zhou, K.; Jubin, R.; Murray, M. G.; Lau, J. Y.; Doudna, J. A. *J. Mol. Biol.* 1999, 292, 513-529; Honda, M.; Beard, M. R.; Ping, L. H.; Lemon, S. M. *J. Virol.* 1999, 73, 1165-1174; Zhao, W. D.; Wimmer, E. *J. Virol.* 2001, 75, 3719-3730, particularly the residues encompassed by the grey shaded area of FIG. 2 as found therein. The stem IIa region of the 5'-UTR of HCV RNA can also be understood as a structure formed by residues 52-65 and residues 102-111 of the HCV RNA (Genbank accession number NC_004102) and naturally occurring variations thereof. It has been surprisingly found that binding to stem region IIa of the 5'-UTR of HCV RNA inhibits replication of HCV. Accordingly, the present invention provides methods for inhibiting HCV replication by contacting HCV with a compound that binds said stem region IIa. In specific embodiments, the methods contemplate binding at concentrations of less than about 50 micromolar (μM). In some particular embodiments, the methods contemplate binding at concentrations of less than about 10 μM.

In some embodiments, compounds according to the invention may be prepared according to the following discussion. In general, compounds according to the present invention selectively bind to HCV IRES. Structure-Activity Relationships (SAR) for a class of compounds may be determined by measuring the $K_D$ for various compounds within the class having a variety of structural features. There are some general rules that guide the artisan in determining whether an active compound is selectively active enough to be considered a candidate for further development (candidate). In this context, it should be recognized that compound that does not qualify as a candidate, nonetheless may have utility as either a positive or negative control in an assay, or may qualify as an assay standard, etc. However, a candidate will generally have an estimated $K_D$ on the order of about 100 μM, will be at least about 4 fold more selective for the target than for non-targets, will generally demonstrate single-site binding, and will be amenable to SAR as a class. For example, for the following Table 1, the target compound (ligand, 50 μM) and IIa target (2.5 μM) were incubated to give the indicated binding percentages of ligand to target.

TABLE 1

| | | | | |
|---|---|---|---|---|
| 56% binding | 15% | 15% | 11% | 6% |

The following Table 2 shows the progression in binding affinity and MS target selectivity for some modifications on the 2-aminobenzimidazole ring.

TABLE 2

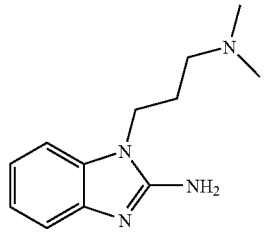

| | | | |
|---|---|---|---|
| Est. $K_D$ (μM) | ~100 | ~40 | ~10 |
| MS target selectivity | ~3 | ~10 | ~15 |

As can be seen in the foregoing Table 2, the selected modifications resulted in an approximately 10-fold improvement in binding affinity and about a 5-fold improvement in target selectivity across the series. As can be seen from the following Table 3, each of the N1, 2- and 6-position substituents are critical for binding to HCV IRES.

TABLE 3

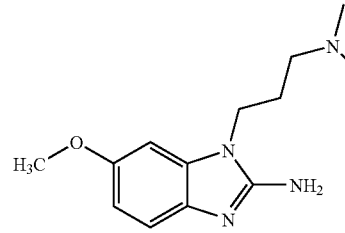

| | | | | |
|---|---|---|---|---|
| Est. $K_D$ (μM) | ~10 | ~100 | >500 | >500 |
| MS Target Selectivity | ~15 | ~3 | ~2 | ~1 |

SAR was performed on the C6-alkyl "tether" (i.e. the alkylene moiety connecting O6 to the amine group. The results for the compounds below are shown in Table 4:

TABLE 4

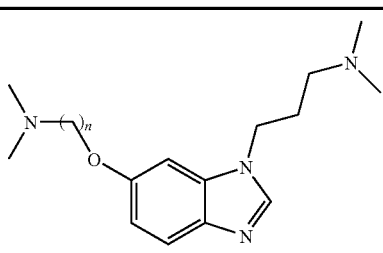

| n | $K_D$(μM) | Target Selectivity |
|---|---|---|
| 2 | 7 | 7 |
| 3 | 9 | 15 |
| 4 | 8 | 11 |

As can be seen above, the $K_D$ at this site is relatively insensitive to tether length, but target selectivity can be improved about 2-fold by selecting n=3 versus n=2.

In the following Table 5, various C-6 side chain modifications are presented, along with their $K_D$ values.
TABLE 5
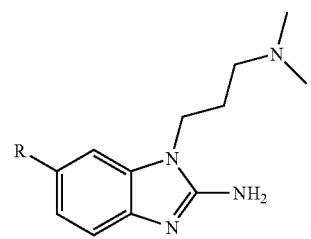
| R | $K_D$ (μM) | R | $K_D$ (μM) |
|---|---|---|---|
|  | 3.6 |  | 2.3 |
|  | 4.6 |  | 3.4 |
|  | 3.7 |  | 7.1 |
|  | 0.71 |  | 2.2 |
|  | 5.5 |  | 0.66 |
|  | 0.78 |  | 0.44 |

TABLE 5-continued

| R | $K_D$ (μM) | R | $K_D$ (μM) |
|---|---|---|---|
| (pyrrolidinone-piperidine-propyloxy) | 2.6 | (2-aminopiperidine-propyloxy) | 0.74 |
| (2-hydroxypyrrolidine-piperidine-propyloxy) | 2.7 | (2-hydroxypyrrolidine-piperidine-propyloxy) | 2.3 |
| (2-aminopyrrolidine-piperidine-propyloxy) | 0.78 | (2-aminopyrrolidine-piperidine-propyloxy) | 0.83 |
| (benzylpyrrolidinyl-amino-propyloxy) | 1.0 | (benzylpyrrolidinyl-amino-propyloxy) | 1.9 |
| (benzylpyrrolidinyl-N-methylamino-propyloxy) | 3.1 | (benzylpyrrolidinyl-amino-propyloxy) | 2.2 |
| (pyrrolidin-3-ylamino-propyloxy) | 0.49 | (pyrrolidin-3-ylamino-propyloxy) | 2.6 |

TABLE 5-continued

| R | $K_D$ (μM) | R | $K_D$ (μM) |
|---|---|---|---|
| (O-propyl-NH-pyrrolidine-N-benzoyl) | 2.2 | (O-propyl-NH-pyrrolidine-NH) | 0.66 |
| (O-propyl-NH-pyrrolidine-N-SO2-phenyl) | 4.5 | (O-propyl-NH-pyrrolidine-N-CH2-pyridyl) | 2.3 |
| (O-propyl-NH-pyrrolidine-N-(4,5-dimethylfuran)) | 1.8 | (O-propyl-NH-piperidine-N-benzyl) | 0.51 |
| (O-propyl-pyrrolidine-OH) | 2.7 | (O-propyl-pyrrolidine-OH) | 2.3 |
| (O-propyl-pyrrolidine-NH2) | 0.78 | (O-propyl-pyrrolidine-NH2) | 0.83 |
| (O-propyl-NH-pyrrolidine-N-benzyl) | 1.0 | | |

Further SAR was performed at the 6-Position on the N- of the (4-aminobutoxy) group. The results of this SAR are shown in Table 6 below:

TABLE 6

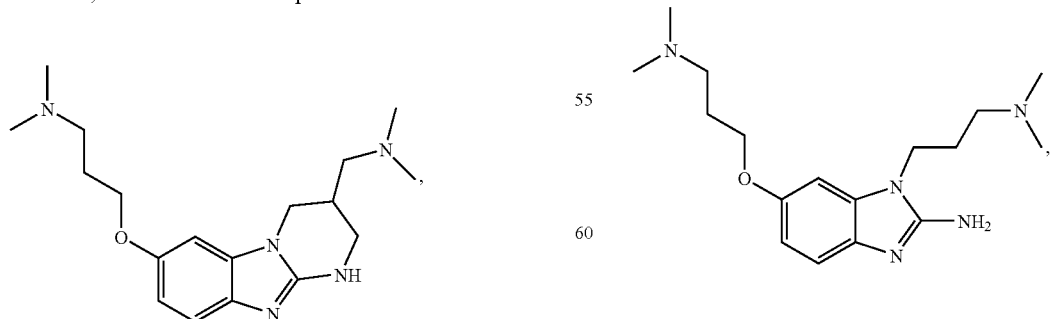

| R | $K_D$ (μM) | R | $K_D$ (μM) | R | $K_D$ (μM) |
|---|---|---|---|---|---|
| CH3 | 3.2 | furan | 2.14 | pyrrole-NH | 2.1 |
| 5-Br-furan | 5.6 | 3-Br-pyrrole-NH | 5.8 | 5-methyl-furan | 4.4 |
| 5-CH2OH-furan | 5.4 | indole-NH | 8.5 | benzofuran | 6.5 |
| pyridine | 4.4 | 5-phenyl-furan | 6.5 | quinoline | 21 |

In order to probe the effect of constraining the N1 and N2 side chains, the constrained compound:

which had a $K_D$ of 0.67 μM, as compared to a $K_D$ of 3.6 μM for the unconstrained compound:

It would appear from the foregoing observation that the constrained N2 side chain has favorable binding characteristics. Accordingly, it was hypothesized that N1-N2 constrained compounds could be identified having improved properties by probing the SAR of 6-position substitutions having a shared constrained core. The results of this study are presented in Table 7 below:

TABLE 7

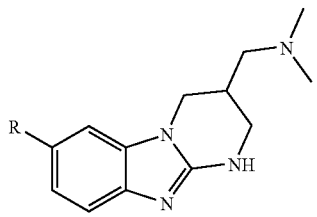

| R | $K_D$ (μM) | R | $K_D$ (μM) |
|---|---|---|---|
| 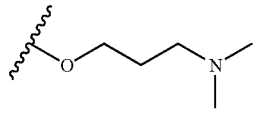 | 0.67 | 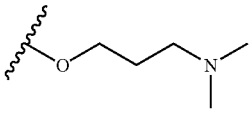 | 0.35 |
| 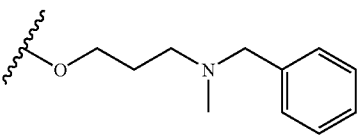 | 0.43 | 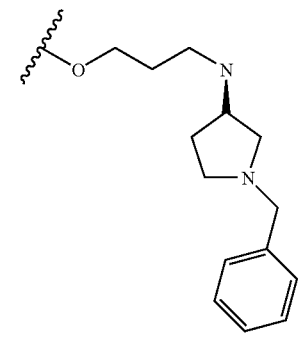 | 0.53 |

Example 19

Replicon Assay

The Ntat2ANeo replicon containing cell line was obtained from Dr. S. Lemon at the University of Galvaston. Cells were grown, handled, treated with compound, and evaluated for HCV RNA levels as described previously (Yi, M.; Bodola, F.; Lemon, S. M. *Virology* 2002, 304, 197-210.) Briefly, the Ntat2ANeo cells were seeded into 96-well plates. The media was replaced 24 h later with fresh, G418-free media containing the indicated concentrations of drug. After the appropriate incubation period, cells were harvested, and quantitative RT-PCR assays were carried out using TaqMan chemistry on a PRISM 7700 instrument (ABI). For detection and quantitation of HCV RNA, primers complementary to the 5'-NTR region of HCV (Takeuchi, T., Katsume, A., Tanaka, T., Abe, A., Inoue, K., Tsukiyama-Kohara, K., Kawaguchi, R., Tanaka, S., and Kohara, M. *Gastroenterology* 1999, 116, 636-642.) were used. Results were normalized to the estimated total RNA content of the sample, as determined by the abundance of cellular GAPDH mRNA detected in a similar real-time RT-PCR assay using reagents provided with Taq-Man GAPDH Control Reagents (Human) (Applied Biosystems).

Example 20

MTT Toxicity Assay

The MTT cell proliferation assay was used to test our compounds for cell toxicity (v van de Loosdrecht, A. A.; Beelen, R. H.; Ossenkoppele, G. J.; Broekhoven, M. G.; Langenhuijsen, M. M. *J. Immunol. Methods* 1994, 174, 311-320. The assay kit was purchased from American Type Culture Collection (Manassas, Va., USA), and treatment of cells and the specific assay protocol was carried out according to the manufacturer's recommendations. The MTT cell proliferation assay measures cell viability and growth by the reduction of tetrazolium salts. The yellow tetrazolium salt is reduced in metabolically active cells to form purple formazan crystals which are solubilized by the addition of detergent. The color was quantified by spectrophotometric means. For each cell type a linear relationship between cell number and absorbance is established, enabling quantification of changes of proliferation.

Compounds according to the present invention were subjected to a replicon assay as described in example 19, as well as an MMT assay as described in example 20. Advantageous compounds according to embodiments of the present invention include, but are not limited to, those listed in Table 8.

TABLE 8

| Compound | Kd to IIa target (μM) | Replicon IC$_{50}$ (μM) | MTT CC$_{50}$ (μM); time (h) |
|---|---|---|---|
| IBIS00403514 | 3.8 | 37.1 | |
| IBIS00408169 | 4.5 | 28.7 | >100 (48) |
| IBIS00528633 | 4.0 | 13.7 | >100 (48) |

TABLE 8-continued
| Compound | Kd to IIa target (μM) | Replicon IC$_{50}$ (μM) | MTT CC$_{50}$ (μM); time (h) |
| --- | --- | --- | --- |
| 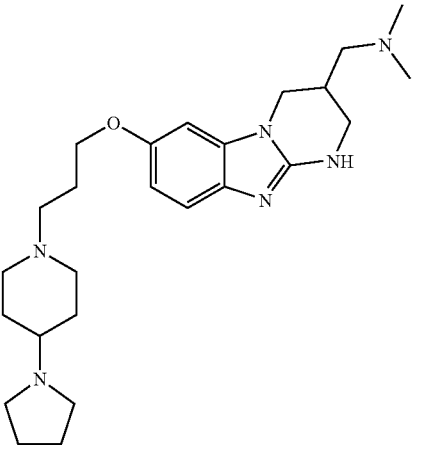<br>IBIS00528634 | 1.7 | 19.2 | >100 (48) |
| 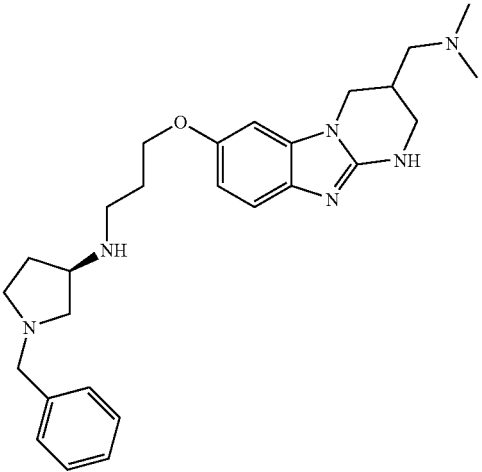<br>IBIS00528635 | 1 | 42.3 | 90 (48) |
| 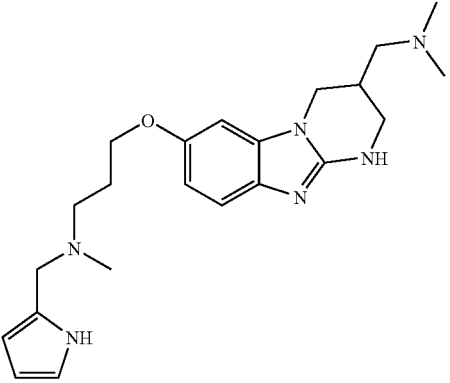<br>IBIS00528636 | 1.2 | 27.2 | 90 (48) |

TABLE 8-continued
| Compound | Kd to IIa target (μM) | Replicon IC$_{50}$ (μM) | MTT CC$_{50}$ (μM); time (h) |
| --- | --- | --- | --- |
| 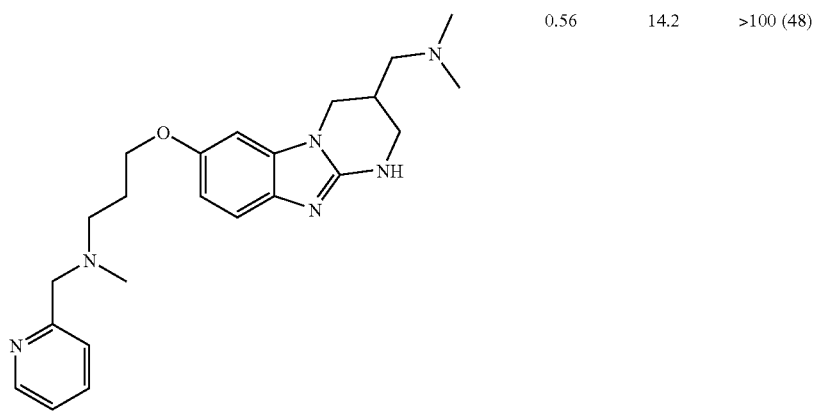 IBIS00528637 | 0.56 | 14.2 | >100 (48) |
| 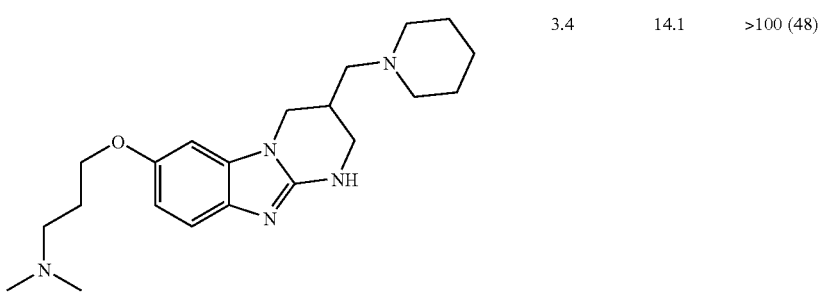 IBIS00554807 | 3.4 | 14.1 | >100 (48) |
| 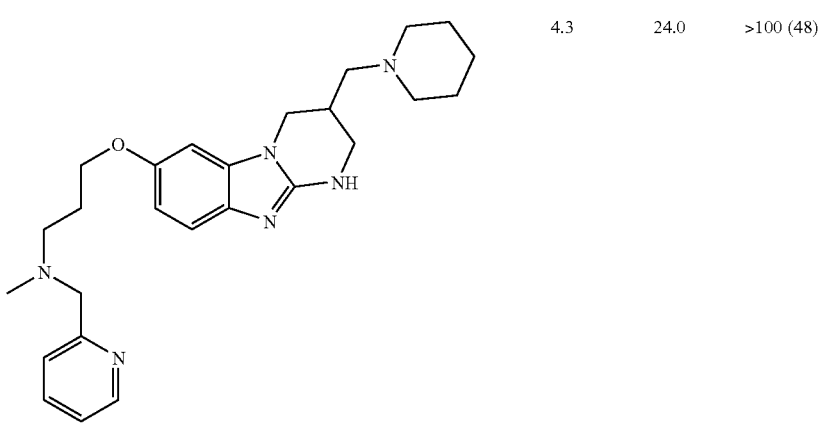 IBIS00554811 | 4.3 | 24.0 | >100 (48) |

TABLE 8-continued
| Compound | Kd to IIa target (μM) | Replicon IC$_{50}$ (μM) | MTT CC$_{50}$ (μM); time (h) |
|---|---|---|---|
| 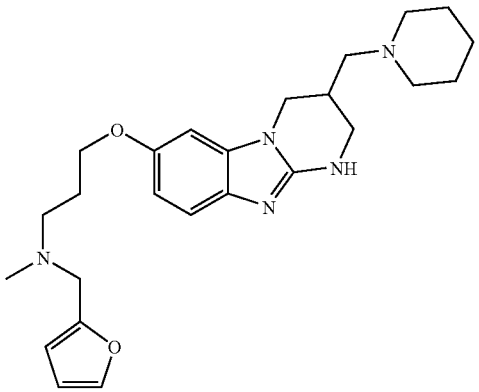 IBIS00554813 | 5.1 | 18.2 | >100 (48) |
| 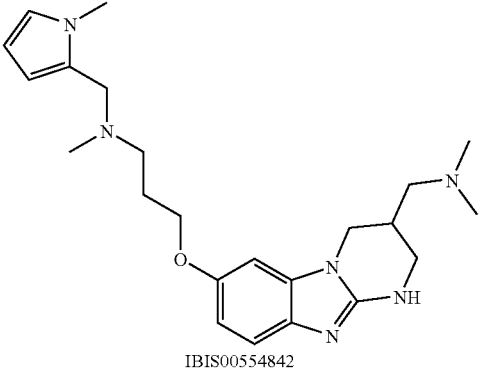 IBIS00554842 | 0.78 | 4.0 | 50 (48) |
| 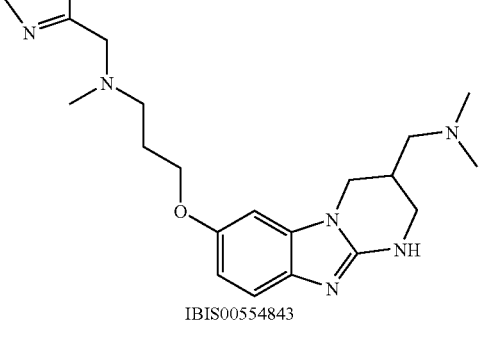 IBIS00554843 | 3.1 | >100 | >100 (48) |
| 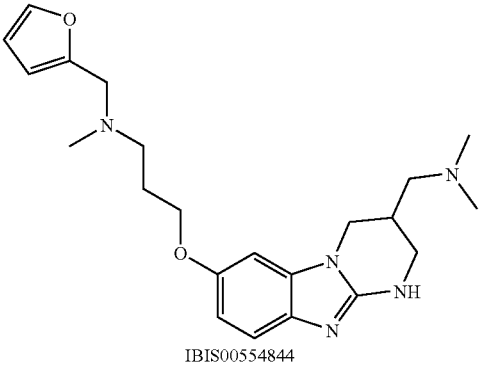 IBIS00554844 | 1.7 | 4.9 | >100 (48) |

TABLE 8-continued
| Compound | Kd to IIa target (μM) | Replicon IC$_{50}$ (μM) | MTT CC$_{50}$ (μM); time (h) |
|---|---|---|---|
| 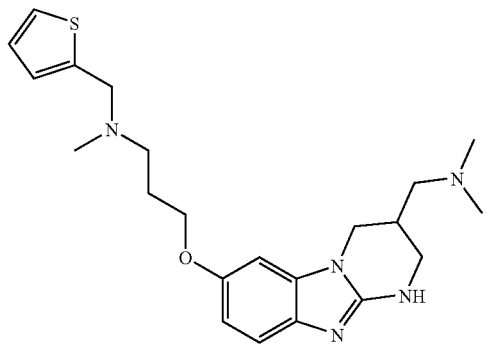<br>IBIS00554886 | 5 | 15.3 | >100 (48) |
| 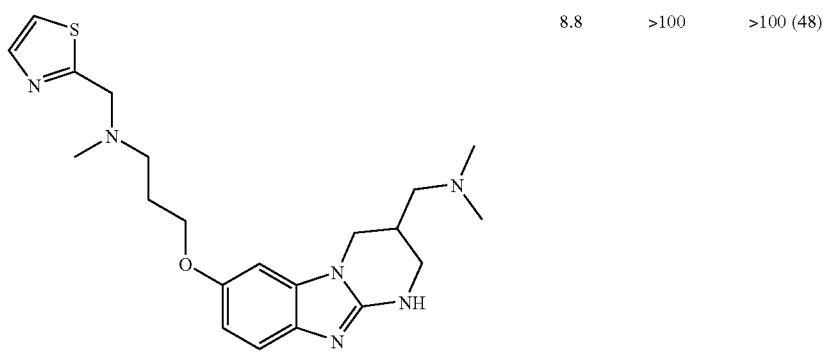<br>IBIS00554888 | 8.8 | >100 | >100 (48) |
| IBIS00554889 | 5.9 | 57.9 | >100 (48) |

TABLE 8-continued
| Compound | Kd to IIa target (μM) | Replicon IC$_{50}$ (μM) | MTT CC$_{50}$ (μM); time (h) |
| --- | --- | --- | --- |
| 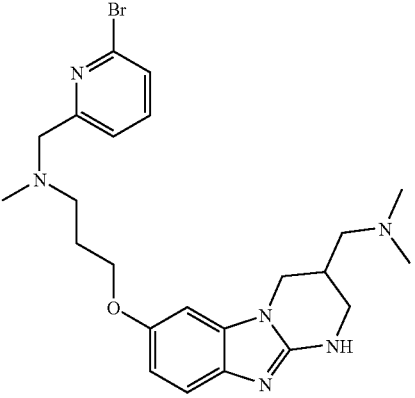<br>IBIS00560002 | 110 | 11.6 | >100 (48) |
| 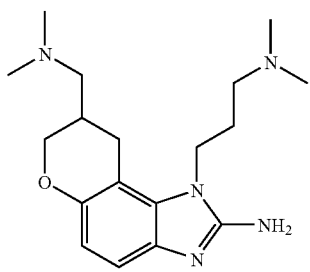<br>IBIS00560020 | 2.2 | 9.0 | >100 (48) |
| 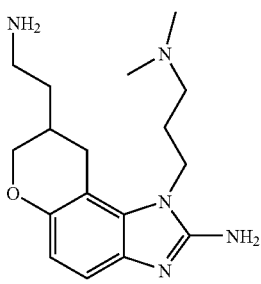<br>IBIS00560024 | 3.4 | >100 | >100 (48) |
| 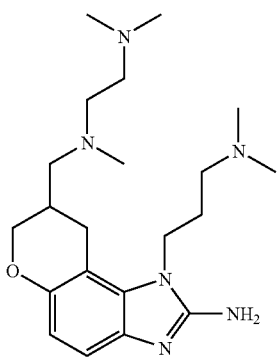<br>IBIS00560025 | 9.4 | 71.2 | >100 (48) |

TABLE 8-continued

| Compound | Kd to IIa target (μM) | Replicon IC$_{50}$ (μM) | MTT CC$_{50}$ (μM); time (h) |
|---|---|---|---|
| IBIS00560031 | 18 | 21.7 | >100 (48) |
| IBIS00560047 | 2.1 | 1.5 | >100 (48) |
| IBIS00560048 | 11 | 23.0 | >100 (48) |
| IBIS00560100 | 3.1 | 51.6 | >100 (48) |

TABLE 8-continued
| Compound | Kd to IIa target (μM) | Replicon IC$_{50}$ (μM) | MTT CC$_{50}$ (μM); time (h) |
|---|---|---|---|
| 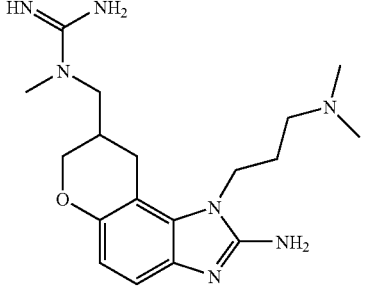<br>IBIS00560101 | 5.5 | >100 | >100 (48) |
| 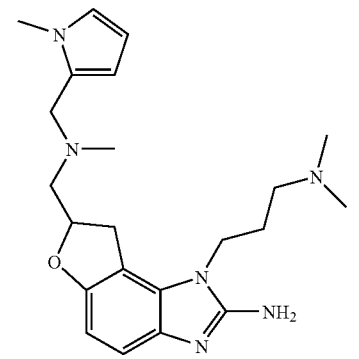<br>IBIS00560102 | 10.4 | 3.3 | >100 (48) |
| 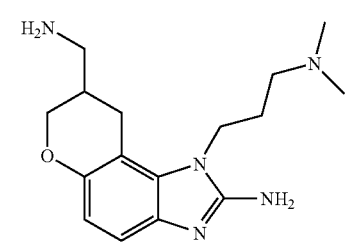<br>IBIS00560121 | 17.2 | 42.7 | >100 (48) |
| 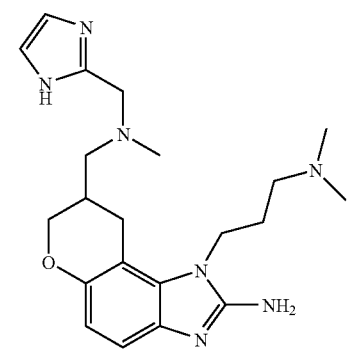<br>IBIS00560122 | 19.6 | >100 | >100 (48) |

TABLE 8-continued

| Compound | Kd to IIa target (μM) | Replicon IC$_{50}$ (μM) | MTT CC$_{50}$ (μM); time (h) |
|---|---|---|---|
| IBIS00560146 | 21.1 | 5.4 | >100 (48) |

Example 21

Acute In Vivo Toxicity Study

A single dose toxicity study was performed to investigate the toxicity of representative compounds. Briefly, 3-4 female mice per group were administered 0, 5, or 45 mg/kg drug (intraperitoneal) on consecutive days for 3 days. At the end of the study, mice were sacrificed, and clinical signs, body weights, clinical pathology, organ weights, and histopathology endpoints were evaluated. Representative compounds were found to exert no obvious toxic effects at pharmacologically relevant doses. The data is summarized in Table 9. The gross findings at necropsy were minor and limited to discolorations in liver and kidney or large gallbladder in 4/18 mice (no dose response and unclear relationship to drug). The organ weights showed no effects. There were no drug-related effects on clinical pathology.

TABLE 9

| Structure | Ibis Number | Clinical Signs |
|---|---|---|
| 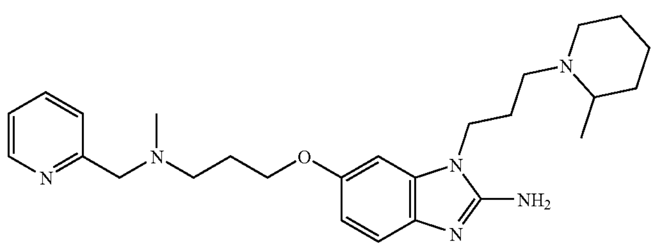 | IBIS00553642 | No significant toxicity at 5 and 45 mg/kg doses. |
| 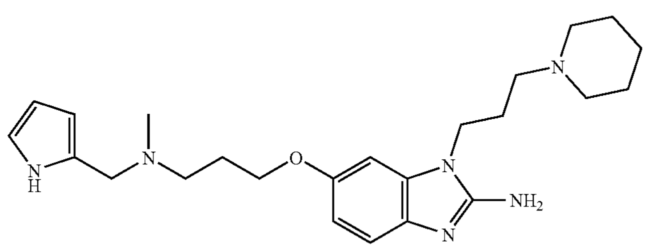 | IBIS00408094 | No significant toxicity at 5 and 45 mg/kg doses. |
| 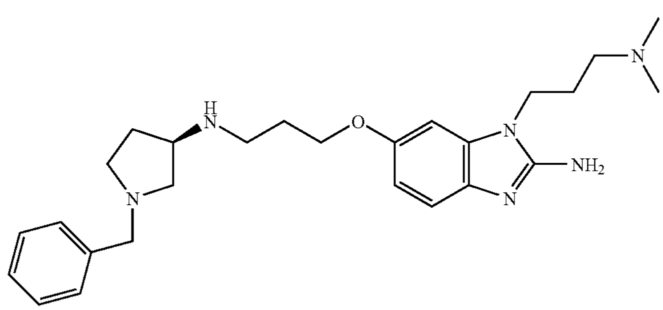 | IBIS00405746 | No significant toxicity at 5 mg/kg dose. |

Example 22

Single Dose In Vivo Pharmacokinetic Study

Figure 2:
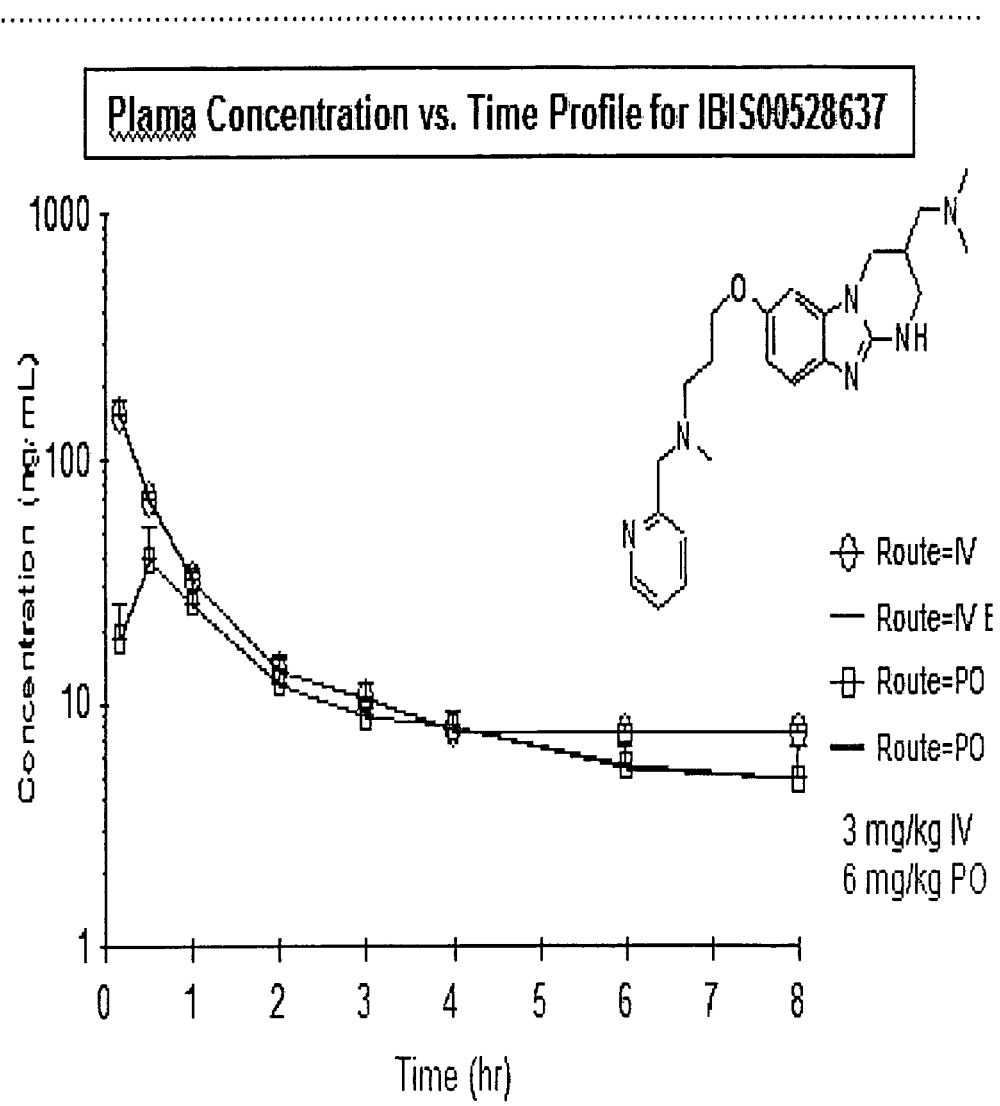
FIG. 2 is a graph of plasma concentration over time for the compound having designation IBIS00528637, according to the depicted chemical structure. This graph further differentiates between routes of administration.

A single dose pharmacokinetic study was performed to investigate the pharmacokinetics of representative compounds. Of particular interest was the ability of the compounds to accumulate in liver, which is the target tissue for HCV chemotherapy as it is the primary reservoir of virus. 3-4 rats per group were administered a single dose (3 mg/kg intravenously, IV or 6 mg/kg orally, PO). Blood samples were taken at 0.25, 0.5, 1, 2, 3, 4, 6, and 8 h timepoints, and pharmacokinetic parameters calculated. The data is summarized in Table 10. Both representative compounds were rapidly distributed to tissues, as evidenced by the high clearance rates and volumes of distribution, and low levels of excretion (ca 10% of total drug in urine and feces at 8 h). Major tissues were examined for presence of drug. Liver, kidney, and lung showed the highest concentration, with liver concentrations achieving ca 8 μg/g tissue 8 h after a single 3 mg/kg IV dose. The tissue accumulation for the IV dose is shown in FIG. 1, as a function of concentration and percent of total administered dose. Oral bioavailability was also studied, and both compounds showed ca 25% oral plasma bioavailability. The plasma concentration vs. time profile for both IV and PO dosing routes for a representative compound is shown in FIG. 2. This data provides that the compounds described herein are present in target tissues, including liver, following oral administration to show an antiviral effect in vivo.

TABLE 10

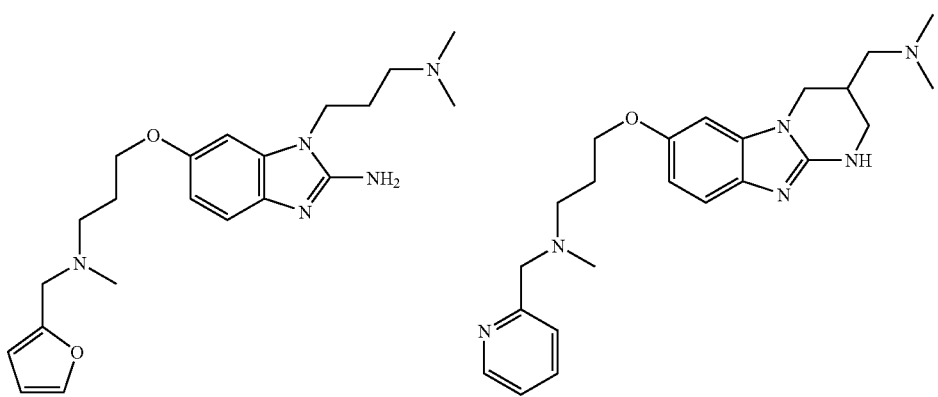

| | | IBIS00405678 | | IBIS00528637 | |
|---|---|---|---|---|---|
| Parameter | Units | Mean | % CV | Mean | % CV |
| Original Dose | mg/kg | 3.0 | | 3.0 | |
| AUC | ng*Hours/ml | 311 | 21.3 | 165 | 2.9 |
| AUC Extrap | ng*Hours/ml | 1928 | 51.2 | 320 | 19.0 |
| Co | ng/ml | 201 | 11.4 | 219 | 10.0 |
| T1/2 | Hours | 37.5 | 55.4 | 14 | 43.8 |
| MRT | Hours | 3.1 | 5.8 | 2 | 5.6 |
| CL | mL/hr/kg | 2069 | 72.6 | 9585 | 17.1 |
| Vdss | mL/kg | 82806 | 22.9 | 136706 | 29.5 |
| % AUC Extrap | % | 80.0 | 14.6 | 47 | 21.8 |

Each of the patents, applications, and printed publications, including books, mentioned in this patent document is hereby incorporated by reference in its entirety. This application further relates to provisional Ser. No. 60/429,595 filed Nov. 26, 2002, now PCT application bearing the same title and is incorporated herein by reference in its entirety.

As those skilled in the art will appreciate, numerous changes and modifications may be made to the preferred embodiments of the invention without departing from the spirit of the invention. It is intended that all such variations fall within the scope of the invention.

We claim:

1. A method of inhibiting HCV replication comprising: providing a compound of the formula:

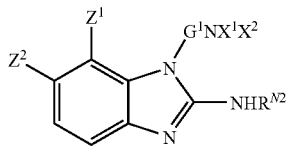

wherein:
G$^1$ is alkylene; R$^{N2}$ joins together with a carbon atom in G$^1$ to form a pyrimidine ring; each of X$^1$ and X$^2$ is independently H or alkyl, or X$^1$ and X$^2$ together form a heterocyclic ring, or X$^1$ together with a carbon atom in G$^1$ forms a cyclic group not fused with the pyrimidine ring, and X$^2$ is H or alkyl; and Z$^1$ and Z$^2$ together form a pyran ring; and administering an amount of said compound or pharmaceutically acceptable salts thereof to a subject wherein said subject is in need of treatment of HCV.

2. The method of claim 1, wherein said method further comprises obtaining an HCV titer of said subject.

3. The method of claim 1, wherein said subject is an animal.

4. The method of claim 1, wherein said subject is a mammal.

5. The method of claim 1, wherein said subject is a human.

6. The method of claim 1, wherein said compound is administered to said subject in an anti-HCV effective amount.

7. A compound having the following formula:

wherein:
G$^1$ is alkylene; R$^{N2}$ joins together with a carbon atom in G$^1$ to form a pyrimidine ring; each of X$^1$ and X$^2$ is independently H or alkyl, or X$^1$ and X$^2$ together form a heterocyclic ring, or X$^1$ together with G$^1$ forms a cyclic group not fused with the pyrimidine ring, and X$^2$ is H or alkyl; and Z$^1$ and Z$^2$ together form a pyran ring; and pharmaceutically acceptable salts thereof.

8. The compound of claim 7, having the formula:

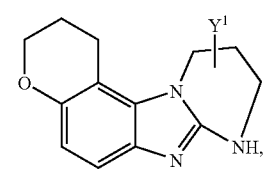

wherein:

Y$^1$ is Ak$^3$NR$^{N3}$R$^{N4}$ or NR$^{N3}$R$^{N4}$, wherein Ak$^3$ is alkylenyl, R$^{N3}$ is H or alkyl R$^{N4}$ is H or alkyl, or together R$^{N3}$ and R$^{N4}$ form a cyclic moiety.

9. A compound having the following structure:

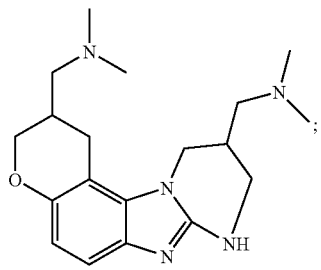

and pharmaceutically acceptable salts thereof.

10. A method comprising administering to a subject a compound of claim 7 wherein said method is performed orally, intraperitonealy or intravenously.

11. A method comprising administering to a subject an amount of the compound according to claim 7 effective to reduce the viral load of HCV in the subject wherein said method is performed orally, intraperitonealy or intravenously.

12. A method of affecting HCV replication comprising:
  contacting a region of a HCV RNA with a pharmaceutical composition comprising a compound according to claim 7, wherein said region of the HCV RNA is region IIa of the HCV IRES; and
  affecting thereby replication of said HCV.

13. The method according to claim 12 wherein region IIa includes residues 52-65 and residues 102-111 of the HCV RNA 5-UTR.

14. A method of affecting HCV replication comprising:
  contacting a region IIa of a HCV RNA with a pharmaceutical composition comprising a compound according to claim 7, having a binding affinity for said region of <50 µM; and
  affecting thereby replication of said HCV.

15. The method according to claim 14 wherein the region is IIa of the HCV RNA 5-UTR and includes residues 52-65 and residues 102-111 of the HCV RNA 5-UTR.

16. A method of affecting HCV replication in vitro comprising:
  contacting in vitro a region of a HCV RNA with a pharmaceutical composition comprising a compound according to claim 7 having a binding affinity for said region of <50 µM, wherein said region of the HCV RNA is region IIa and has a stem secondary structure; and
  affecting thereby replication of said HCV.

17. A method of affecting HCV replication in vivo comprising:
  contacting in vivo a region of a HCV RNA with a pharmaceutical composition comprising a compound according to claim 7 having a binding affinity for said region of <50 µM, wherein said region of the HCV RNA is region IIa and includes residues 52-65 and residues 102-111 of the HCV RNA 5-UTR; and
  affecting thereby replication of said HCV.

18. A method comprising:
  contacting a region of a HCV RNA wherein said region of the HCV RNA is region IIa and has a stem secondary structure and includes residues 52-65 and residues 102-111 of the HCV RNA 5-UTR with a pharmaceutical composition comprising a compound according to claim 7; and
  quantifying the affect of the pharmaceutical composition on HCV replication.

19. The method according to claim 18 wherein said contacting is in vivo.

20. The method according to claim 18 wherein said contacting is in vitro.

* * * * *